(12) United States Patent
Merritt et al.

(10) Patent No.: US 11,865,291 B2
(45) Date of Patent: Jan. 9, 2024

(54) HEMOSTASIS VALVES AND METHODS OF USE

(71) Applicant: Inari Medical, Inc., Irvine, CA (US)

(72) Inventors: Benjamin E. Merritt, San Clemente, CA (US); John C. Thress, Capistrano Beach, CA (US); Paul Lubock, Monarch Beach, CA (US)

(73) Assignee: Inari Medical, Inc., Irvine, CA (US)

( * ) Notice: Subject to any disclaimer, the term of this patent is extended or adjusted under 35 U.S.C. 154(b) by 0 days.

(21) Appl. No.: 18/142,518

(22) Filed: May 2, 2023

(65) Prior Publication Data

US 2023/0270991 A1   Aug. 31, 2023

Related U.S. Application Data

(60) Division of application No. 17/705,189, filed on Mar. 25, 2022, now Pat. No. 11,697,011, which is a
(Continued)

(51) Int. Cl.
*A61M 39/06* (2006.01)
*A61B 17/3207* (2006.01)

(52) U.S. Cl.
CPC ..... *A61M 39/0613* (2013.01); *A61B 17/3207* (2013.01); *A61M 2039/062* (2013.01); *A61M 2039/0673* (2013.01)

(58) Field of Classification Search
CPC ............ A61M 2039/062; A61M 39/06; A61M 2039/0626; A61M 2039/0673;
(Continued)

(56) References Cited

U.S. PATENT DOCUMENTS

| 1,101,890 A | 6/1914 | Tunstead |
| 2,784,717 A | 3/1957 | Thompson |

(Continued)

FOREIGN PATENT DOCUMENTS

| AU | 2015210338 | 8/2015 |
| CN | 102186427 | 9/2011 |

(Continued)

OTHER PUBLICATIONS

European Patent Application No. 13838945.7, Extended European Search Report, 9 pages, dated Apr. 15, 2016.
(Continued)

*Primary Examiner* — Quynh-Nhu H. Vu
(74) *Attorney, Agent, or Firm* — Perkins Coie LLP

(57) ABSTRACT

Devices, systems, and methods for sealing medical devices, particularly during intravascular access, are disclosed herein. Some aspects relate to a hemostatic valve for sealing a wide range of medical devices, such as catheters, wires, embolectomy systems. The valve can include an elongate member having a first end, a second end, and a central lumen extending therebetween. A reinforcement structure extends along at least a portion of the elongate member and is coupled to the elongate member. A shell defining a first aperture and a second aperture may be included, which first and second apertures can be fluidly coupled by the elongate member. A tensioning mechanism is coupled to the shell and to the elongate member, the tensioning mechanism can be moveable between a first configuration wherein the tensioning mechanism is collapsed and the central lumen is sealed and a second configuration wherein the central lumen is open.

20 Claims, 10 Drawing Sheets

Related U.S. Application Data continuation of application No. 17/226,318, filed on Apr. 9, 2021, which is a continuation of application No. 16/117,519, filed on Aug. 30, 2018, now Pat. No. 11,000,682.

(60) Provisional application No. 62/554,931, filed on Sep. 6, 2017.

(58) Field of Classification Search
CPC ........ A61M 39/0613; F16K 7/06; F16K 7/04; F16K 7/08; F16K 7/02
See application file for complete search history.

(56) References Cited

U.S. PATENT DOCUMENTS

| | | |
|---|---|---|
| 2,846,179 A | 8/1958 | Monckton |
| 2,955,592 A | 10/1960 | Maclean |
| 3,088,363 A | 5/1963 | Sparks |
| 3,197,173 A | 7/1965 | Taubenheim |
| 3,416,531 A | 12/1968 | Edwards |
| 3,435,826 A | 4/1969 | Fogarty |
| 3,438,607 A | 4/1969 | Williams et al. |
| 3,515,137 A | 6/1970 | Santomieri |
| 3,675,657 A * | 7/1972 | Gauthier .............. A61B 17/132 606/203 |
| 3,860,006 A | 1/1975 | Patel |
| 3,892,161 A | 7/1975 | Sokol |
| 3,923,065 A | 12/1975 | Nozick et al. |
| 4,030,503 A | 6/1977 | Clark, III |
| 4,034,642 A | 7/1977 | Tannucci et al. |
| 4,222,380 A | 9/1980 | Terayama |
| 4,243,040 A | 1/1981 | Beecher |
| 4,287,808 A | 9/1981 | Leonard et al. |
| 4,324,262 A | 4/1982 | Hall |
| 4,393,872 A | 7/1983 | Reznik et al. |
| 4,401,107 A | 8/1983 | Harber et al. |
| 4,469,100 A | 9/1984 | Hardwick |
| 4,523,738 A | 6/1985 | Raftis et al. |
| 4,551,862 A * | 11/1985 | Haber .................. A61F 2/0036 600/491 |
| 4,604,094 A | 8/1986 | Shook |
| 4,611,594 A | 9/1986 | Grayhack et al. |
| 4,634,421 A | 1/1987 | Hegemann |
| 4,643,184 A | 2/1987 | Mobin-Uddin |
| 4,646,736 A | 3/1987 | Auth et al. |
| 4,650,466 A | 3/1987 | Luther |
| 4,776,337 A | 10/1988 | Palmaz |
| 4,790,812 A | 12/1988 | Hawkins, Jr. et al. |
| 4,863,440 A | 9/1989 | Chin et al. |
| 4,870,953 A | 10/1989 | DonMichael et al. |
| 4,883,458 A | 11/1989 | Shiber |
| 4,886,062 A | 12/1989 | Wiktor |
| 4,890,611 A | 1/1990 | Monfort et al. |
| 4,898,575 A | 2/1990 | Fischell et al. |
| 4,946,440 A | 8/1990 | Hall |
| 4,960,259 A | 10/1990 | Sunnanvader et al. |
| 4,978,341 A | 12/1990 | Niederhauser |
| 4,981,478 A | 1/1991 | Evard et al. |
| 5,030,201 A | 7/1991 | Palestrant |
| 5,059,178 A | 10/1991 | Ya |
| 5,100,423 A | 3/1992 | Fearnot |
| 5,127,626 A | 7/1992 | Hilal et al. |
| 5,129,910 A | 7/1992 | Phan et al. |
| 5,135,484 A | 8/1992 | Wright |
| 5,154,724 A | 10/1992 | Andrews |
| 5,158,533 A | 10/1992 | Strauss et al. |
| 5,158,564 A | 10/1992 | Schnepp-Pesch et al. |
| 5,192,274 A | 3/1993 | Bierman |
| 5,192,286 A | 3/1993 | Phan et al. |
| 5,192,290 A | 3/1993 | Hilal |
| 5,197,485 A | 3/1993 | Grooters |
| 5,234,403 A | 8/1993 | Yoda et al. |
| 5,242,461 A | 9/1993 | Kortenbach et al. |
| 5,244,619 A | 9/1993 | Burnham |
| 5,329,923 A | 7/1994 | Lundquist |
| 5,360,417 A | 11/1994 | Gravener et al. |
| 5,364,345 A | 11/1994 | Lowery et al. |
| 5,376,101 A | 12/1994 | Green et al. |
| 5,383,887 A | 1/1995 | Nadal |
| 5,389,100 A | 2/1995 | Bacich et al. |
| 5,391,152 A | 2/1995 | Patterson et al. |
| 5,419,774 A | 5/1995 | Willard et al. |
| 5,421,824 A | 6/1995 | Clement et al. |
| 5,443,443 A | 8/1995 | Shiber |
| 5,456,667 A | 10/1995 | Ham et al. |
| 5,476,450 A | 12/1995 | Ruggio |
| 5,484,418 A | 1/1996 | Quiachon et al. |
| 5,490,859 A | 2/1996 | Mische et al. |
| 5,496,365 A | 3/1996 | Sgro |
| 5,527,326 A | 6/1996 | Hermann et al. |
| 5,549,626 A | 8/1996 | Miller et al. |
| 5,591,137 A | 1/1997 | Stevens |
| 5,639,276 A | 6/1997 | Weinstock et al. |
| 5,653,684 A | 8/1997 | Laptewicz et al. |
| 5,662,703 A | 9/1997 | Yurek et al. |
| 5,746,758 A | 5/1998 | Nordgren et al. |
| 5,749,858 A | 5/1998 | Cramer |
| 5,769,816 A | 6/1998 | Barbut et al. |
| 5,782,817 A | 7/1998 | Franzel et al. |
| 5,800,457 A | 9/1998 | Gelbfish |
| 5,827,229 A | 10/1998 | Auth et al. |
| 5,846,251 A | 12/1998 | Hart |
| 5,860,938 A | 1/1999 | Lafontaine et al. |
| 5,873,866 A | 2/1999 | Kondo et al. |
| 5,873,882 A | 2/1999 | Straub et al. |
| 5,876,414 A | 3/1999 | Straub |
| 5,895,406 A | 4/1999 | Gray et al. |
| 5,908,435 A | 6/1999 | Samuels |
| 5,911,710 A | 6/1999 | Barry et al. |
| 5,911,733 A | 6/1999 | Parodi |
| 5,911,754 A | 6/1999 | Kanesaka et al. |
| 5,941,869 A | 8/1999 | Patterson et al. |
| 5,947,985 A | 9/1999 | Imram |
| 5,954,737 A | 9/1999 | Lee |
| 5,971,938 A | 10/1999 | Hart et al. |
| 5,971,958 A | 10/1999 | Zhang |
| 5,972,019 A | 10/1999 | Engelson et al. |
| 5,974,938 A | 11/1999 | Lloyd |
| 5,989,233 A | 11/1999 | Yoon |
| 5,993,483 A | 11/1999 | Gianotti |
| 6,017,335 A | 1/2000 | Burnham |
| 6,030,397 A | 2/2000 | Moneti et al. |
| 6,059,814 A | 5/2000 | Ladd |
| 6,066,158 A | 5/2000 | Engelson et al. |
| 6,068,645 A | 5/2000 | Tu |
| 6,126,635 A | 10/2000 | Simpson et al. |
| 6,142,987 A | 11/2000 | Tsugita |
| 6,146,396 A | 11/2000 | Konya et al. |
| 6,146,403 A | 11/2000 | St. Germain |
| 6,152,144 A | 11/2000 | Lesh et al. |
| 6,152,946 A | 11/2000 | Broome et al. |
| 6,156,055 A | 12/2000 | Ravenscroft |
| 6,159,230 A | 12/2000 | Samuels |
| 6,165,196 A | 12/2000 | Stack et al. |
| 6,168,579 B1 | 1/2001 | Tsugita |
| 6,179,859 B1 | 1/2001 | Bates et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,245,078 B1 | 6/2001 | Ouchi |
| 6,245,089 B1 | 6/2001 | Daniel et al. |
| 6,254,571 B1 | 7/2001 | Hart |
| 6,258,115 B1 | 7/2001 | Dubrul |
| 6,264,663 B1 | 7/2001 | Cano |
| 6,306,163 B1 | 10/2001 | Fitz |
| 6,322,572 B1 | 11/2001 | Lee |
| 6,350,271 B1 | 2/2002 | Kurz et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,402,771 B1 | 6/2002 | Palmer et al. |
| 6,413,235 B1 | 7/2002 | Parodi |

(56) References Cited

U.S. PATENT DOCUMENTS

| | | |
|---|---|---|
| 6,423,032 B2 | 7/2002 | Parodi |
| 6,432,122 B1 | 8/2002 | Gilson et al. |
| 6,451,036 B1 | 9/2002 | Heitzmann et al. |
| 6,458,103 B1 | 10/2002 | Albert et al. |
| 6,475,236 B1 | 11/2002 | Roubin et al. |
| 6,485,502 B2 | 11/2002 | Don Michael |
| 6,508,782 B1 | 1/2003 | Evans et al. |
| 6,511,492 B1 | 1/2003 | Rosenbluth et al. |
| 6,514,273 B1 | 2/2003 | Voss et al. |
| 6,530,923 B1 | 3/2003 | Dubrul et al. |
| 6,530,935 B2 | 3/2003 | Wensel et al. |
| 6,540,722 B1 | 4/2003 | Boyle et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,551,342 B1 | 4/2003 | Shen et al. |
| 6,564,828 B1 | 5/2003 | Ishida |
| 6,569,181 B1 | 5/2003 | Burns |
| 6,575,995 B1 | 6/2003 | Huter et al. |
| 6,589,263 B1 | 7/2003 | Hopkins et al. |
| 6,596,011 B2 | 7/2003 | Johnson et al. |
| 6,602,271 B2 | 8/2003 | Adams et al. |
| 6,605,074 B2 | 8/2003 | Zadno-azizi et al. |
| 6,605,102 B1 | 8/2003 | Mazzocchi et al. |
| 6,610,077 B1 | 8/2003 | Hancock et al. |
| 6,620,148 B1 | 9/2003 | Tsugita |
| 6,620,179 B2 | 9/2003 | Brook et al. |
| 6,620,182 B1 | 9/2003 | Khosravi et al. |
| 6,623,460 B1 | 9/2003 | Heck |
| 6,635,068 B1 | 10/2003 | Dubrul et al. |
| 6,645,222 B1 | 11/2003 | Parodi et al. |
| 6,660,013 B2 | 12/2003 | Rabiner et al. |
| 6,660,014 B2 | 12/2003 | Demarais et al. |
| 6,663,650 B2 | 12/2003 | Sepetka et al. |
| 6,692,504 B2 | 2/2004 | Kurz et al. |
| 6,699,260 B2 | 3/2004 | Dubrul et al. |
| 6,702,830 B1 | 3/2004 | Demarais et al. |
| 6,719,717 B1 | 4/2004 | Johnson et al. |
| 6,755,847 B2 | 6/2004 | Eskuri |
| 6,767,353 B1 | 7/2004 | Shiber |
| 6,790,204 B2 | 9/2004 | Zadno-Azizi et al. |
| 6,800,080 B1 | 10/2004 | Bates |
| 6,818,006 B2 | 11/2004 | Douk et al. |
| 6,824,545 B2 | 11/2004 | Sepetka et al. |
| 6,824,550 B1 | 11/2004 | Noriega et al. |
| 6,824,553 B1 | 11/2004 | Gene et al. |
| 6,830,561 B2 | 12/2004 | Jansen et al. |
| 6,846,029 B1 | 1/2005 | Ragner et al. |
| 6,902,540 B2 | 6/2005 | Dorros et al. |
| 6,939,361 B1 | 9/2005 | Kleshinski |
| 6,942,682 B2 | 9/2005 | Vrba et al. |
| 6,945,977 B2 | 9/2005 | Demarais et al. |
| 6,960,189 B2 | 11/2005 | Bates et al. |
| 6,960,222 B2 | 11/2005 | Vo et al. |
| 7,004,931 B2 | 2/2006 | Hogendijk |
| 7,004,954 B1 | 2/2006 | Voss et al. |
| 7,036,707 B2 | 5/2006 | Aota et al. |
| 7,041,084 B2 | 5/2006 | Fotjik |
| 7,052,500 B2 | 5/2006 | Bashiri et al. |
| 7,056,328 B2 | 6/2006 | Arnott |
| 7,063,707 B2 | 6/2006 | Bose et al. |
| 7,069,835 B2 | 7/2006 | Nishri et al. |
| 7,094,249 B1 | 8/2006 | Thomas et al. |
| 7,122,034 B2 | 10/2006 | Belhe et al. |
| 7,128,073 B1 | 10/2006 | van der Burg et al. |
| 7,152,605 B2 | 12/2006 | Khairkhahan et al. |
| 7,179,273 B1 | 2/2007 | Palmer et al. |
| 7,223,253 B2 | 5/2007 | Hogendijk |
| 7,232,432 B2 | 6/2007 | Fulton, III et al. |
| 7,244,243 B2 | 7/2007 | Lary |
| 7,285,126 B2 | 10/2007 | Sepetka et al. |
| 7,300,458 B2 | 11/2007 | Henkes et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,980 B2 | 2/2008 | Dubrul et al. |
| 7,481,805 B2 | 1/2009 | Magnusson |
| 7,534,234 B2 | 5/2009 | Fotjik |
| 7,578,830 B2 | 8/2009 | Kusleika et al. |
| 7,621,870 B2 | 11/2009 | Berrada et al. |
| 7,674,247 B2 | 3/2010 | Fotjik |
| 7,678,131 B2 | 3/2010 | Muller |
| 7,691,121 B2 | 4/2010 | Rosenbluth et al. |
| 7,695,458 B2 | 4/2010 | Belley et al. |
| 7,713,282 B2 | 5/2010 | Frazier et al. |
| 7,722,641 B2 | 5/2010 | van der Burg et al. |
| 7,763,010 B2 | 7/2010 | Evans et al. |
| 7,766,934 B2 | 8/2010 | Pal et al. |
| 7,775,501 B2 * | 8/2010 | Kees .................. F16K 7/065 |
| | | 251/5 |
| 7,780,696 B2 | 8/2010 | Daniel et al. |
| 7,815,608 B2 | 10/2010 | Schafersman et al. |
| 7,905,877 B1 | 3/2011 | Oscar et al. |
| 7,905,896 B2 | 3/2011 | Straub |
| 7,938,809 B2 | 5/2011 | Lampropoulos et al. |
| 7,938,820 B2 | 5/2011 | Webster et al. |
| 7,967,790 B2 | 6/2011 | Whiting et al. |
| 7,976,511 B2 | 7/2011 | Fotjik |
| 7,993,302 B2 | 8/2011 | Hebert et al. |
| 7,993,363 B2 | 8/2011 | Demond et al. |
| 8,021,351 B2 | 9/2011 | Boldenow et al. |
| 8,043,313 B2 | 10/2011 | Krolik et al. |
| 8,052,640 B2 | 11/2011 | Fiorella et al. |
| 8,057,496 B2 | 11/2011 | Fischer, Jr. |
| 8,057,497 B1 | 11/2011 | Raju et al. |
| 8,066,757 B2 | 11/2011 | Ferrera et al. |
| 8,070,694 B2 | 12/2011 | Galdonik et al. |
| 8,070,769 B2 | 12/2011 | Broome |
| 8,070,791 B2 | 12/2011 | Ferrera et al. |
| 8,075,510 B2 | 12/2011 | Aklog et al. |
| 8,080,032 B2 | 12/2011 | van der Burg et al. |
| 8,088,140 B2 | 1/2012 | Ferrera et al. |
| 8,092,486 B2 | 1/2012 | Berrada et al. |
| 8,100,935 B2 | 1/2012 | Rosenbluth et al. |
| 8,109,962 B2 | 2/2012 | Pal |
| 8,118,829 B2 | 2/2012 | Carrison et al. |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fotjik |
| RE43,902 E | 1/2013 | Hopkins et al. |
| 8,343,167 B2 | 1/2013 | Henson |
| 8,357,178 B2 | 1/2013 | Grandfield et al. |
| 8,361,104 B2 | 1/2013 | Jones et al. |
| 8,409,215 B2 | 4/2013 | Sepetka et al. |
| 8,480,708 B2 | 7/2013 | Kassab et al. |
| 8,486,105 B2 | 7/2013 | Demond et al. |
| 8,491,539 B2 | 7/2013 | Fotjik |
| 8,512,352 B2 | 8/2013 | Martin |
| 8,523,897 B2 | 9/2013 | van der Burg et al. |
| 8,535,283 B2 | 9/2013 | Heaton et al. |
| 8,535,334 B2 | 9/2013 | Martin |
| 8,535,343 B2 | 9/2013 | van der Burg et al. |
| 8,545,526 B2 | 10/2013 | Martin et al. |
| 8,568,432 B2 | 10/2013 | Straub |
| 8,568,465 B2 | 10/2013 | Freudenthal et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,754 B2 | 12/2013 | Wensel et al. |
| 8,647,367 B2 | 2/2014 | Kassab et al. |
| 8,657,867 B2 | 2/2014 | Dorn et al. |
| 8,696,622 B2 | 4/2014 | Fiorella et al. |
| 8,715,314 B1 | 5/2014 | Janardhan et al. |
| 8,721,714 B2 | 5/2014 | Kelley |
| 8,753,322 B2 | 6/2014 | Hu et al. |
| 8,771,289 B2 | 7/2014 | Mohiuddin et al. |
| 8,777,893 B2 | 7/2014 | Malewicz |
| 8,784,441 B2 | 7/2014 | Rosenbluth et al. |
| 8,784,442 B2 | 7/2014 | Jones et al. |
| 8,784,469 B2 | 7/2014 | Kassab |

(56) References Cited

U.S. PATENT DOCUMENTS

| | | |
|---|---|---|
| 8,795,305 B2 | 8/2014 | Martin et al. |
| 8,795,345 B2 | 8/2014 | Grandfield et al. |
| 8,801,748 B2 | 8/2014 | Martin |
| 8,808,259 B2 | 8/2014 | Walton et al. |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,834,519 B2 | 9/2014 | van der Burg et al. |
| 8,845,621 B2 | 9/2014 | Fotjik |
| 8,852,226 B2 | 10/2014 | Gilson et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 8,992,504 B2 | 3/2015 | Castella et al. |
| 9,005,172 B2 | 4/2015 | Chung |
| 9,011,551 B2 | 4/2015 | Oral et al. |
| 9,028,401 B1 | 5/2015 | Bacich et al. |
| 9,078,682 B2 | 7/2015 | Lenker et al. |
| 9,101,382 B2 | 8/2015 | Krolik et al. |
| 9,125,683 B2 | 9/2015 | Farhangnia et al. |
| 9,126,016 B2 | 9/2015 | Fulton |
| 9,149,609 B2 | 10/2015 | Ansel et al. |
| 9,155,552 B2 | 10/2015 | Ulm, III |
| 9,161,766 B2 | 10/2015 | Slee et al. |
| 9,168,043 B2 | 10/2015 | van der Burg et al. |
| 9,173,668 B2 | 11/2015 | Ulm, III |
| 9,186,487 B2 | 11/2015 | Dubrul et al. |
| 9,204,887 B2 | 12/2015 | Cully et al. |
| 9,216,277 B2 | 12/2015 | Myers |
| 9,241,669 B2 | 1/2016 | Pugh et al. |
| 9,358,037 B2 | 1/2016 | Farhangnia et al. |
| 9,259,237 B2 | 2/2016 | Quick et al. |
| 9,265,512 B2 | 2/2016 | Carrison et al. |
| 9,283,066 B2 | 3/2016 | Hopkins et al. |
| 9,301,769 B2 | 4/2016 | Brady et al. |
| 9,351,747 B2 | 5/2016 | Kugler et al. |
| 9,439,664 B2 | 9/2016 | Sos |
| 9,439,751 B2 | 9/2016 | White et al. |
| 9,456,834 B2 | 10/2016 | Folk |
| 9,463,035 B1 | 10/2016 | Greenhalgh et al. |
| 9,463,036 B2 | 10/2016 | Brady et al. |
| 9,526,864 B2 | 12/2016 | Quick |
| 9,526,865 B2 | 12/2016 | Quick |
| 9,532,792 B2 | 1/2017 | Galdonik et al. |
| 9,566,073 B2 | 2/2017 | Kassab et al. |
| 9,566,424 B2 | 2/2017 | Pessin |
| 9,579,116 B1 | 2/2017 | Nguyen et al. |
| 9,581,942 B1 | 2/2017 | Shippert |
| 9,616,213 B2 | 4/2017 | Furnish et al. |
| 9,636,206 B2 | 5/2017 | Nguyen et al. |
| 9,643,035 B2 | 5/2017 | Mastenbroek |
| 9,662,129 B2 | 5/2017 | Galdonik et al. |
| 9,700,332 B2 | 7/2017 | Marchand et al. |
| 9,717,488 B2 | 8/2017 | Kassab et al. |
| 9,717,514 B2 | 8/2017 | Martin et al. |
| 9,717,519 B2 | 8/2017 | Rosenbluth et al. |
| 9,744,024 B2 | 8/2017 | Nguyen et al. |
| 9,757,137 B2 | 9/2017 | Krolik et al. |
| 9,827,084 B2 | 11/2017 | Bonnette et al. |
| 9,844,386 B2 | 12/2017 | Nguyen et al. |
| 9,844,387 B2 | 12/2017 | Marchand et al. |
| 9,848,975 B2 | 12/2017 | Hauser |
| 9,849,014 B2 | 12/2017 | Kusleika |
| 9,884,387 B2 | 2/2018 | Plha |
| 9,962,178 B2 | 5/2018 | Greenhalgh et al. |
| 9,980,813 B2 * | 5/2018 | Eller .................. F16K 7/06 |
| 9,999,493 B2 | 6/2018 | Nguyen et al. |
| 10,004,531 B2 | 6/2018 | Rosenbluth et al. |
| 10,010,335 B2 | 7/2018 | Greenhalgh et al. |
| 10,016,266 B2 | 7/2018 | Hauser |
| 10,028,759 B2 | 7/2018 | Wallace et al. |
| 10,045,790 B2 | 8/2018 | Cox et al. |
| 10,058,339 B2 | 8/2018 | Galdonik et al. |
| 10,098,651 B2 | 10/2018 | Marchand et al. |
| 10,130,385 B2 | 11/2018 | Farhangnia et al. |
| 10,183,159 B2 * | 1/2019 | Nobles .................. A61M 39/22 |
| 10,226,263 B2 | 3/2019 | Look et al. |
| 10,238,406 B2 | 3/2019 | Cox et al. |
| 10,271,864 B2 | 4/2019 | Greenhalgh et al. |
| 10,327,883 B2 | 6/2019 | Yachia |
| 10,335,186 B2 | 7/2019 | Rosenbluth et al. |
| 10,342,571 B2 | 7/2019 | Marchand et al. |
| 10,349,960 B2 | 7/2019 | Quick |
| 10,383,644 B2 | 8/2019 | Molaei et al. |
| 10,384,034 B2 | 8/2019 | Carrison et al. |
| 10,456,555 B2 | 10/2019 | Carrison et al. |
| 10,478,535 B2 | 11/2019 | Ogle |
| 10,485,952 B2 | 11/2019 | Carrison et al. |
| 10,524,811 B2 | 1/2020 | Marchand et al. |
| 10,531,883 B1 | 1/2020 | Deville et al. |
| 10,588,655 B2 | 3/2020 | Rosenbluth et al. |
| 10,648,268 B2 | 5/2020 | Jaffrey et al. |
| 10,695,159 B2 | 6/2020 | Hauser |
| 10,709,471 B2 | 7/2020 | Rosenbluth et al. |
| 10,772,636 B2 | 9/2020 | Kassab et al. |
| 10,799,331 B2 | 10/2020 | Hauser |
| 10,912,577 B2 | 2/2021 | Marchand et al. |
| 10,926,060 B2 | 2/2021 | Stern et al. |
| 10,953,195 B2 | 3/2021 | Jalgaonkar et al. |
| 10,960,114 B2 | 3/2021 | Goisis |
| 11,000,682 B2 | 5/2021 | Merritt et al. |
| 11,013,523 B2 | 5/2021 | Arad Hadar |
| 11,058,445 B2 | 7/2021 | Cox et al. |
| 11,058,451 B2 | 7/2021 | Marchand et al. |
| 11,065,019 B1 | 7/2021 | Chou et al. |
| 11,147,571 B2 | 10/2021 | Cox et al. |
| 11,154,314 B2 | 10/2021 | Quick |
| 11,166,703 B2 | 11/2021 | Kassab et al. |
| 11,185,664 B2 | 11/2021 | Carrison et al. |
| 11,224,450 B2 | 1/2022 | Chou et al. |
| 11,224,721 B2 | 1/2022 | Carrison et al. |
| 11,259,821 B2 | 3/2022 | Buck et al. |
| 11,305,094 B2 | 4/2022 | Carrison et al. |
| 11,383,064 B2 | 7/2022 | Carrison et al. |
| 11,395,903 B2 | 7/2022 | Carrison et al. |
| 11,433,218 B2 | 9/2022 | Quick et al. |
| 11,439,799 B2 | 9/2022 | Buck et al. |
| 11,457,936 B2 | 10/2022 | Buck et al. |
| 11,529,158 B2 | 12/2022 | Hauser |
| 11,554,005 B2 | 1/2023 | Merritt et al. |
| 11,559,382 B2 | 1/2023 | Merritt et al. |
| 11,576,691 B2 | 2/2023 | Chou et al. |
| 11,596,768 B2 | 3/2023 | Stern et al. |
| 11,642,209 B2 | 5/2023 | Merritt et al. |
| 11,648,028 B2 | 5/2023 | Rosenbluth et al. |
| 11,697,011 B2 | 7/2023 | Merritt et al. |
| 11,697,012 B2 | 7/2023 | Merritt et al. |
| 11,744,691 B2 | 9/2023 | Merritt et al. |
| 11,806,033 B2 | 11/2023 | Marchand et al. |
| 2001/0004699 A1 | 6/2001 | Gittings et al. |
| 2001/0031981 A1 | 10/2001 | Evans et al. |
| 2001/0041909 A1 | 11/2001 | Tsugita et al. |
| 2001/0049486 A1 | 12/2001 | Evans et al. |
| 2001/0051810 A1 | 12/2001 | Dubrul et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0032455 A1 | 3/2002 | Boock et al. |
| 2002/0049452 A1 | 4/2002 | Kurz et al. |
| 2002/0095161 A1 | 7/2002 | Dhindsa |
| 2002/0095171 A1 | 7/2002 | Belef |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0151918 A1 | 10/2002 | Lafontaine et al. |
| 2002/0156457 A1 | 10/2002 | Fisher |
| 2002/0161392 A1 | 10/2002 | Dubrul |
| 2002/0169474 A1 | 11/2002 | Kusleika |
| 2002/0173819 A1 | 11/2002 | Leeflang et al. |
| 2002/0188276 A1 | 12/2002 | Evans et al. |
| 2003/0023263 A1 | 1/2003 | Krolik et al. |

(56) References Cited

U.S. PATENT DOCUMENTS

| | | |
|---|---|---|
| 2003/0083693 A1 | 5/2003 | Daniel et al. |
| 2003/0100919 A1 | 5/2003 | Hopkins et al. |
| 2003/0114875 A1 | 6/2003 | Sjostrom |
| 2003/0116731 A1 | 6/2003 | Hartley |
| 2003/0125663 A1* | 7/2003 | Coleman ............ A61M 25/0136 604/95.04 |
| 2003/0135151 A1 | 7/2003 | Deng |
| 2003/0135230 A1 | 7/2003 | Massey et al. |
| 2003/0135258 A1 | 7/2003 | Andreas et al. |
| 2003/0153873 A1 | 8/2003 | Luther et al. |
| 2003/0153973 A1 | 8/2003 | Soun et al. |
| 2003/0168068 A1 | 9/2003 | Poole et al. |
| 2003/0176884 A1 | 9/2003 | Berrada et al. |
| 2003/0191516 A1 | 10/2003 | Weldon et al. |
| 2003/0208224 A1 | 11/2003 | Broome |
| 2003/0216774 A1 | 11/2003 | Larson |
| 2004/0019310 A1 | 1/2004 | Hogendijk |
| 2004/0039351 A1 | 2/2004 | Barrett |
| 2004/0039412 A1 | 2/2004 | Isshiki et al. |
| 2004/0068288 A1 | 4/2004 | Palmer et al. |
| 2004/0073243 A1 | 4/2004 | Sepetka et al. |
| 2004/0098033 A1 | 5/2004 | Leeflang et al. |
| 2004/0102807 A1 | 5/2004 | Kusleika et al. |
| 2004/0122359 A1 | 6/2004 | Wenz et al. |
| 2004/0127936 A1 | 7/2004 | Salahieh et al. |
| 2004/0133232 A1 | 7/2004 | Rosenbluth et al. |
| 2004/0138525 A1 | 7/2004 | Saadat et al. |
| 2004/0138692 A1 | 7/2004 | Phung et al. |
| 2004/0167567 A1 | 8/2004 | Cano et al. |
| 2004/0199201 A1 | 10/2004 | Kellett et al. |
| 2004/0199202 A1 | 10/2004 | Dubrul et al. |
| 2004/0260344 A1 | 12/2004 | Lyons et al. |
| 2004/0267272 A1 | 12/2004 | Henniges et al. |
| 2005/0004534 A1 | 1/2005 | Lockwood et al. |
| 2005/0033172 A1 | 2/2005 | Dubrul et al. |
| 2005/0038468 A1 | 2/2005 | Panetta et al. |
| 2005/0054995 A1 | 3/2005 | Barzell et al. |
| 2005/0055047 A1 | 3/2005 | Greenhalgh |
| 2005/0085769 A1 | 4/2005 | MacMahon et al. |
| 2005/0085826 A1 | 4/2005 | Nair et al. |
| 2005/0085846 A1 | 4/2005 | Carrison et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1 | 8/2005 | Nguyen et al. |
| 2005/0203605 A1 | 9/2005 | Dolan |
| 2005/0283165 A1 | 12/2005 | Gadberry |
| 2005/0283166 A1 | 12/2005 | Greenhalgh et al. |
| 2005/0283186 A1 | 12/2005 | Berrada et al. |
| 2006/0020286 A1 | 1/2006 | Niermann |
| 2006/0042786 A1 | 3/2006 | West |
| 2006/0047286 A1 | 3/2006 | West |
| 2006/0074401 A1 | 4/2006 | Ross |
| 2006/0089533 A1 | 4/2006 | Ziegler et al. |
| 2006/0100662 A1 | 5/2006 | Daniel et al. |
| 2006/0155305 A1 | 7/2006 | Freudenthal et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0217664 A1 | 9/2006 | Hattler et al. |
| 2006/0224177 A1 | 10/2006 | Finitsis |
| 2006/0229645 A1 | 10/2006 | Bonnette et al. |
| 2006/0247500 A1 | 11/2006 | Voegele et al. |
| 2006/0253145 A1 | 11/2006 | Lucas |
| 2006/0264905 A1 | 11/2006 | Eskridge et al. |
| 2006/0276874 A1 | 12/2006 | Wilson et al. |
| 2006/0282111 A1 | 12/2006 | Morsi |
| 2006/0293696 A1 | 12/2006 | Fahey et al. |
| 2007/0010787 A1 | 1/2007 | Hackett et al. |
| 2007/0038225 A1 | 2/2007 | Osborne |
| 2007/0093744 A1 | 4/2007 | Elmaleh |
| 2007/0112374 A1 | 5/2007 | Paul, Jr. et al. |
| 2007/0118165 A1 | 5/2007 | DeMello et al. |
| 2007/0149996 A1 | 6/2007 | Coughlin |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0213765 A1 | 9/2007 | Adams et al. |
| 2007/0233043 A1 | 10/2007 | Dayton et al. |
| 2007/0255252 A1 | 11/2007 | Mehta |
| 2007/0288054 A1 | 12/2007 | Tanaka et al. |
| 2008/0015541 A1 | 1/2008 | Rosenbluth et al. |
| 2008/0087853 A1 | 4/2008 | Kees |
| 2008/0088055 A1 | 4/2008 | Ross |
| 2008/0157017 A1 | 7/2008 | Macatangay et al. |
| 2008/0167678 A1 | 7/2008 | Morsi |
| 2008/0183136 A1 | 7/2008 | Lenker et al. |
| 2008/0228209 A1 | 9/2008 | DeMello et al. |
| 2008/0234715 A1 | 9/2008 | Pesce et al. |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0300466 A1 | 12/2008 | Gresham |
| 2008/0312681 A1 | 12/2008 | Ansel et al. |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0069828 A1 | 3/2009 | Martin et al. |
| 2009/0076417 A1 | 3/2009 | Jones |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0192495 A1 | 7/2009 | Ostrovsky et al. |
| 2009/0281525 A1 | 11/2009 | Harding et al. |
| 2009/0292307 A1 | 11/2009 | Razack |
| 2009/0299393 A1 | 12/2009 | Martin et al. |
| 2010/0016837 A1 | 1/2010 | Howat |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0087850 A1 | 4/2010 | Razack |
| 2010/0094201 A1 | 4/2010 | Mallaby |
| 2010/0106081 A1 | 4/2010 | Brandeis |
| 2010/0114017 A1 | 5/2010 | Lenker et al. |
| 2010/0114113 A1 | 5/2010 | Dubrul et al. |
| 2010/0121312 A1 | 5/2010 | Gielenz et al. |
| 2010/0137846 A1 | 6/2010 | Desai et al. |
| 2010/0190156 A1 | 7/2010 | Van Wordragen et al. |
| 2010/0204712 A1 | 8/2010 | Mallaby |
| 2010/0217276 A1 | 8/2010 | Garrison et al. |
| 2010/0249815 A1 | 9/2010 | Jantzen et al. |
| 2010/0268264 A1 | 10/2010 | Bonnette et al. |
| 2010/0318178 A1 | 12/2010 | Rapaport et al. |
| 2011/0034986 A1 | 2/2011 | Chou et al. |
| 2011/0034987 A1 | 2/2011 | Kennedy |
| 2011/0054405 A1 | 3/2011 | Whiting et al. |
| 2011/0060212 A1 | 3/2011 | Slee et al. |
| 2011/0071503 A1 | 3/2011 | Takagi et al. |
| 2011/0118817 A1 | 5/2011 | Gunderson et al. |
| 2011/0125181 A1 | 5/2011 | Brady et al. |
| 2011/0144592 A1* | 6/2011 | Wong ................ A61M 39/0613 604/175 |
| 2011/0152823 A1 | 6/2011 | Mohiuddin et al. |
| 2011/0152889 A1 | 6/2011 | Ashland |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |
| 2011/0190806 A1 | 8/2011 | Wittens |
| 2011/0196309 A1 | 8/2011 | Wells |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1 | 10/2011 | Sakata et al. |
| 2011/0251629 A1 | 10/2011 | Galdonik et al. |
| 2011/0264133 A1 | 10/2011 | Hanlon et al. |
| 2011/0265681 A1 | 11/2011 | Allen et al. |
| 2011/0288529 A1 | 11/2011 | Fulton |
| 2011/0288572 A1 | 11/2011 | Martin |
| 2011/0319917 A1 | 12/2011 | Ferrera et al. |

(56) References Cited

U.S. PATENT DOCUMENTS

| | | |
|---|---|---|
| 2012/0059309 A1 | 3/2012 | di Palma et al. |
| 2012/0059356 A1 | 3/2012 | di Palma et al. |
| 2012/0083824 A1 | 4/2012 | Berrada et al. |
| 2012/0083868 A1 | 4/2012 | Shrivastava |
| 2012/0089216 A1 | 4/2012 | Rapaport et al. |
| 2012/0101480 A1 | 4/2012 | Ingle et al. |
| 2012/0101510 A1 | 4/2012 | Lenker et al. |
| 2012/0109109 A1 | 5/2012 | Kajii |
| 2012/0138832 A1 | 6/2012 | Townsend |
| 2012/0143239 A1 | 6/2012 | Aklog et al. |
| 2012/0165919 A1 | 6/2012 | Cox et al. |
| 2012/0172918 A1 | 7/2012 | Fifer et al. |
| 2012/0179181 A1 | 7/2012 | Straub et al. |
| 2012/0197277 A1 | 8/2012 | Stinis |
| 2012/0232655 A1 | 9/2012 | Lorrison et al. |
| 2012/0271105 A1 | 10/2012 | Nakamura et al. |
| 2012/0271231 A1 | 10/2012 | Agrawal |
| 2012/0277788 A1 | 11/2012 | Cattaneo |
| 2012/0310166 A1 | 12/2012 | Huff |
| 2013/0030460 A1 | 1/2013 | Marks et al. |
| 2013/0035628 A1 | 2/2013 | Garrison et al. |
| 2013/0046332 A1 | 2/2013 | Jones et al. |
| 2013/0066348 A1 | 3/2013 | Fiorella et al. |
| 2013/0092012 A1 | 4/2013 | Marchand et al. |
| 2013/0096571 A1 | 4/2013 | Massicotte et al. |
| 2013/0102996 A1 | 4/2013 | Strauss |
| 2013/0116708 A1 | 5/2013 | Ziniti et al. |
| 2013/0116721 A1 | 5/2013 | Takagi et al. |
| 2013/0126559 A1 | 5/2013 | Cowan et al. |
| 2013/0144326 A1 | 6/2013 | Brady et al. |
| 2013/0150793 A1 | 6/2013 | Beissel et al. |
| 2013/0165871 A1 | 6/2013 | Fiorella et al. |
| 2013/0184703 A1 | 7/2013 | Shireman et al. |
| 2013/0197454 A1 | 8/2013 | Shibata et al. |
| 2013/0197567 A1 | 8/2013 | Brady et al. |
| 2013/0204297 A1 | 8/2013 | Melsheimer et al. |
| 2013/0226196 A1 | 8/2013 | Smith |
| 2013/0281788 A1 | 10/2013 | Garrison |
| 2013/0289608 A1 | 10/2013 | Tanaka et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046133 A1 | 2/2014 | Nakamura et al. |
| 2014/0046243 A1 | 2/2014 | Ray et al. |
| 2014/0052161 A1 | 2/2014 | Cully et al. |
| 2014/0074144 A1 | 3/2014 | Shrivastava et al. |
| 2014/0121672 A1 | 5/2014 | Folk |
| 2014/0155830 A1 | 6/2014 | Bonnette et al. |
| 2014/0155980 A1 | 6/2014 | Turjman |
| 2014/0180055 A1 | 6/2014 | Glynn et al. |
| 2014/0180397 A1 | 6/2014 | Gerberding et al. |
| 2014/0155908 A1 | 7/2014 | Rosenbluth et al. |
| 2014/0188127 A1 | 7/2014 | Dubrul et al. |
| 2014/0188143 A1 | 7/2014 | Martin et al. |
| 2014/0222070 A1 | 8/2014 | Belson et al. |
| 2014/0236219 A1 | 8/2014 | Dubrul et al. |
| 2014/0243882 A1 | 8/2014 | Ma |
| 2014/0257253 A1 | 9/2014 | Jemison |
| 2014/0257363 A1 | 9/2014 | Lippert |
| 2014/0276403 A1 | 9/2014 | Follmer et al. |
| 2014/0296868 A1 | 10/2014 | Garrison et al. |
| 2014/0303658 A1 | 10/2014 | Bonnette et al. |
| 2014/0318354 A1 | 10/2014 | Thompson et al. |
| 2014/0324091 A1 | 10/2014 | Rosenbluth |
| 2014/0330286 A1 | 11/2014 | Wallace et al. |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick |
| 2015/0018860 A1 | 1/2015 | Quick |
| 2015/0018929 A1 | 1/2015 | Martin et al. |
| 2015/0025555 A1 | 1/2015 | Sos |
| 2015/0032144 A1 | 1/2015 | Holloway |
| 2015/0059908 A1 | 3/2015 | Mollen |
| 2015/0088190 A1 | 3/2015 | Jensen |
| 2015/0127035 A1 | 5/2015 | Trapp et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0164666 A1 | 6/2015 | Johnson et al. |
| 2015/0173782 A1 | 6/2015 | Garrison et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0305756 A1 | 10/2015 | Rosenbluth |
| 2015/0305859 A1* | 10/2015 | Eller .................. A61F 2/2469 623/1.24 |
| 2015/0352325 A1 | 12/2015 | Quick |
| 2015/0360001 A1 | 12/2015 | Quick |
| 2015/0374391 A1 | 12/2015 | Quick |
| 2016/0022293 A1 | 1/2016 | Dubrul et al. |
| 2016/0030708 A1 | 2/2016 | Casiello et al. |
| 2016/0038267 A1 | 2/2016 | Allen et al. |
| 2016/0058540 A1 | 3/2016 | Don Michael |
| 2016/0074627 A1 | 3/2016 | Cottone |
| 2016/0106353 A1 | 4/2016 | Schuetz et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0113666 A1 | 4/2016 | Quick |
| 2016/0135829 A1 | 5/2016 | Holochwost et al. |
| 2016/0143721 A1 | 5/2016 | Rosenbluth |
| 2016/0151605 A1 | 6/2016 | Welch et al. |
| 2016/0192912 A1 | 7/2016 | Kassab et al. |
| 2016/0206344 A1 | 7/2016 | Bruzzi et al. |
| 2016/0008014 A1 | 8/2016 | Rosenbluth |
| 2016/0220741 A1 | 8/2016 | Garrison et al. |
| 2016/0228134 A1 | 8/2016 | Martin et al. |
| 2016/0262774 A1 | 9/2016 | Honda |
| 2016/0262790 A1 | 9/2016 | Rosenbluth et al. |
| 2016/0287276 A1 | 10/2016 | Cox et al. |
| 2016/0367285 A1 | 12/2016 | Sos |
| 2017/0014560 A1 | 1/2017 | Minskoff et al. |
| 2017/0021130 A1 | 1/2017 | Dye |
| 2017/0037548 A1 | 2/2017 | Lee |
| 2017/0042571 A1 | 2/2017 | Levi |
| 2017/0049942 A1 | 2/2017 | Conlan et al. |
| 2017/0056032 A1 | 3/2017 | Look et al. |
| 2017/0058623 A1 | 3/2017 | Jaffrey et al. |
| 2017/0079672 A1 | 3/2017 | Quick |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0105745 A1 | 4/2017 | Rosenbluth et al. |
| 2017/0112514 A1 | 4/2017 | Marchand et al. |
| 2017/0143359 A1 | 5/2017 | Nguyen et al. |
| 2017/0143938 A1 | 5/2017 | Ogle et al. |
| 2017/0112513 A1 | 7/2017 | Marchand et al. |
| 2017/0189041 A1 | 7/2017 | Cox et al. |
| 2017/0196576 A1 | 7/2017 | Long et al. |
| 2017/0233908 A1 | 8/2017 | Kroczynski et al. |
| 2017/0252057 A1 | 9/2017 | Bonnette et al. |
| 2017/0265878 A1 | 9/2017 | Marchand et al. |
| 2017/0281204 A1 | 10/2017 | Garrison et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |

(56) References Cited

U.S. PATENT DOCUMENTS

| | | |
|---|---|---|
| 2017/0319221 A1 | 11/2017 | Chu |
| 2017/0325839 A1 | 11/2017 | Rosenbluth et al. |
| 2017/0340867 A1 | 11/2017 | Accisano, II |
| 2017/0348014 A1 | 12/2017 | Wallace et al. |
| 2018/0042623 A1 | 2/2018 | Batiste |
| 2018/0042624 A1 | 2/2018 | Greenhalgh et al. |
| 2018/0042626 A1 | 2/2018 | Greenhalgh et al. |
| 2018/0055999 A1 | 3/2018 | Bare et al. |
| 2018/0064453 A1 | 3/2018 | Garrison et al. |
| 2018/0064454 A1 | 3/2018 | Losordo et al. |
| 2018/0070968 A1 | 3/2018 | Wallace et al. |
| 2018/0092652 A1 | 4/2018 | Marchand et al. |
| 2018/0104404 A1 | 4/2018 | Ngo-Chu |
| 2018/0105963 A1 | 4/2018 | Quick |
| 2018/0125512 A1 | 5/2018 | Nguyen et al. |
| 2018/0184912 A1 | 7/2018 | Al-Ali |
| 2018/0193043 A1 | 7/2018 | Marchand et al. |
| 2018/0236205 A1 | 8/2018 | Krautkremer et al. |
| 2018/0250498 A1 | 9/2018 | Stern et al. |
| 2018/0256177 A1 | 9/2018 | Cooper et al. |
| 2018/0256178 A1 | 9/2018 | Cox et al. |
| 2018/0296240 A1 | 10/2018 | Rosenbluth et al. |
| 2018/0344339 A1 | 12/2018 | Cox et al. |
| 2018/0361116 A1 | 12/2018 | Quick et al. |
| 2019/0000492 A1 | 1/2019 | Casey et al. |
| 2019/0015298 A1 | 1/2019 | Beatty et al. |
| 2019/0046219 A1 | 2/2019 | Marchand et al. |
| 2019/0070401 A1 | 3/2019 | Merritt et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0150959 A1 | 5/2019 | Cox et al. |
| 2019/0231373 A1 | 8/2019 | Quick |
| 2019/0239910 A1 | 8/2019 | Brady et al. |
| 2019/0321071 A1 | 10/2019 | Marchand et al. |
| 2019/0336142 A1 | 11/2019 | Torrie et al. |
| 2019/0336148 A1 | 11/2019 | Greenhalgh et al. |
| 2019/0365395 A1 | 12/2019 | Tran et al. |
| 2019/0366036 A1 | 12/2019 | Jalgaonkar et al. |
| 2020/0022711 A1 | 1/2020 | Look et al. |
| 2020/0046368 A1 | 2/2020 | Merritt et al. |
| 2020/0046940 A1 | 2/2020 | Carrison et al. |
| 2020/0113412 A1 | 4/2020 | Jensen |
| 2020/0121334 A1 | 4/2020 | Galdonik et al. |
| 2021/0022843 A1 | 1/2021 | Hauser |
| 2021/0038385 A1 | 2/2021 | Popp et al. |
| 2021/0113224 A1 | 4/2021 | Dinh |
| 2021/0137667 A1 | 5/2021 | Sonnette et al. |
| 2021/0138194 A1 | 5/2021 | Carrison et al. |
| 2021/0186541 A1 | 6/2021 | Thress |
| 2021/0205577 A1 | 7/2021 | Jalgaonkar et al. |
| 2021/0236148 A1 | 8/2021 | Marchand et al. |
| 2021/0290925 A1 | 9/2021 | Merritt et al. |
| 2021/0315598 A1 | 10/2021 | Buck et al. |
| 2021/0330344 A1 | 10/2021 | Rosenbluth et al. |
| 2021/0378694 A1 | 12/2021 | Thress et al. |
| 2021/0393278 A1 | 12/2021 | O'Malley et al. |
| 2021/0404464 A1 | 12/2021 | Patoskie |
| 2022/0000505 A1 | 1/2022 | Hauser |
| 2022/0000506 A1 | 1/2022 | Hauser |
| 2022/0000507 A1 | 1/2022 | Hauser |
| 2022/0015798 A1 | 1/2022 | Marchand et al. |
| 2022/0022898 A1 | 1/2022 | Cox et al. |
| 2022/0033888 A1 | 2/2022 | Schnall-Levin et al. |
| 2022/0039815 A1 | 2/2022 | Thress et al. |
| 2022/0125451 A1 | 4/2022 | Hauser |
| 2022/0142638 A1 | 5/2022 | Enright et al. |
| 2022/0151647 A1 | 5/2022 | Dolendo et al. |
| 2022/0160381 A1 | 5/2022 | Hauser |
| 2022/0160382 A1 | 5/2022 | Hauser |
| 2022/0160383 A1 | 5/2022 | Hauser |
| 2022/0211400 A1 | 7/2022 | Cox et al. |
| 2022/0211992 A1 | 7/2022 | Merritt et al. |
| 2022/0240959 A1 | 8/2022 | Quick |
| 2022/0346800 A1 | 11/2022 | Merritt et al. |
| 2022/0346801 A1 | 11/2022 | Merritt et al. |
| 2022/0346813 A1 | 11/2022 | Quick |
| 2022/0346814 A1 | 11/2022 | Quick |
| 2022/0347455 A1 | 11/2022 | Merritt et al. |
| 2022/0362512 A1 | 11/2022 | Quick et al. |
| 2022/0370761 A1 | 11/2022 | Chou et al. |
| 2023/0046775 A1 | 2/2023 | Quick |
| 2023/0059721 A1 | 2/2023 | Chou et al. |
| 2023/0062809 A1 | 3/2023 | Merritt et al. |
| 2023/0070120 A1 | 3/2023 | Cox et al. |
| 2023/0122587 A1 | 4/2023 | Chou et al. |
| 2023/0200970 A1 | 6/2023 | Merritt et al. |
| 2023/0218310 A1 | 7/2023 | Scheinblum et al. |
| 2023/0218313 A1 | 7/2023 | Rosenbluth et al. |
| 2023/0218383 A1 | 7/2023 | Merritt et al. |
| 2023/0233311 A1 | 7/2023 | Merritt et al. |
| 2023/0240705 A1 | 8/2023 | Rosenbluth et al. |
| 2023/0240706 A1 | 8/2023 | Rosenbluth et al. |
| 2023/0241302 A1 | 8/2023 | Merritt et al. |
| 2023/0248380 A1 | 8/2023 | Long et al. |
| 2023/0310137 A1 | 10/2023 | Merritt et al. |
| 2023/0310138 A1 | 10/2023 | Merritt et al. |
| 2023/0310751 A1 | 10/2023 | Merritt et al. |
| 2023/0320834 A1 | 10/2023 | Merritt et al. |
| 2023/0329734 A1 | 10/2023 | Marchand et al. |
| 2023/0338130 A1 | 10/2023 | Merritt et al. |
| 2023/0338131 A1 | 10/2023 | Merritt et al. |

FOREIGN PATENT DOCUMENTS

| | | |
|---|---|---|
| CN | 103764049 | 4/2014 |
| CN | 103932756 | 7/2014 |
| CN | 104068910 | 10/2014 |
| CN | 106178227 | 12/2016 |
| CN | 108348319 | 7/2018 |
| CN | 110652645 | 1/2020 |
| CN | 111281482 | 6/2020 |
| DE | 102017004383 | 7/2018 |
| EP | 1254634 | 11/2002 |
| EP | 1867290 | 2/2013 |
| EP | 2942624 | 11/2015 |
| EP | 3583972 | 12/2019 |
| EP | 3589348 | 1/2020 |
| EP | 3620204 | 3/2020 |
| EP | 3013404 | 4/2020 |
| EP | 4137070 | 2/2023 |
| GB | 1588072 | 4/1981 |
| GB | 2498349 | 7/2013 |
| JP | H6190049 | 7/1994 |
| JP | H07323090 A | 12/1995 |
| JP | 2001522631 | 5/1999 |
| JP | 2004097807 | 4/2004 |
| JP | 2005-095242 | 6/2005 |
| JP | 2005230132 | 9/2005 |
| JP | 2005323702 | 11/2005 |
| JP | 2006094876 | 4/2006 |
| JP | 2011526820 | 1/2010 |
| WO | WO1997017889 | 5/1997 |
| WO | WO199833443 | 8/1998 |
| WO | WO199838920 | 9/1998 |
| WO | WO199839053 | 9/1998 |
| WO | WO199851237 | 11/1998 |
| WO | WO1999044542 | 9/1999 |
| WO | WO2000032118 | 6/2000 |
| WO | WO2000053120 | 9/2000 |
| WO | WO0202162 | 1/2002 |
| WO | WO2003015840 | 2/2003 |
| WO | WO2004018916 | 3/2004 |
| WO | WO2004093696 | 11/2004 |
| WO | WO2005046736 | 5/2005 |
| WO | WO2006029270 | 3/2006 |
| WO | WO2006110186 | 10/2006 |
| WO | WO2006124307 | 11/2006 |
| WO | WO2007092820 | 8/2007 |
| WO | WO2009082513 | 7/2009 |

(56) References Cited

FOREIGN PATENT DOCUMENTS

| | | |
|---|---|---|
| WO | WO2009086482 | 7/2009 |
| WO | WO2009155571 | 12/2009 |
| WO | WO2010002549 | 1/2010 |
| WO | WO2010010545 | 1/2010 |
| WO | WO2010023671 | 3/2010 |
| WO | WO2010049121 | 5/2010 |
| WO | WO2010102307 | 9/2010 |
| WO | WO2011032712 | 3/2011 |
| WO | WO2011054531 | 5/2011 |
| WO | WO2011073176 | 6/2011 |
| WO | WO2012009675 | 1/2012 |
| WO | WO2012011097 | 1/2012 |
| WO | WO2012049652 | 4/2012 |
| WO | WO2012065748 | 5/2012 |
| WO | WO2012120490 | 9/2012 |
| WO | WO2012162437 | 11/2012 |
| WO | WO2014047650 | 3/2014 |
| WO | WO2014081892 | 5/2014 |
| WO | WO2015006782 | 1/2015 |
| WO | WO2015061365 | 4/2015 |
| WO | WO2015121424 | 8/2015 |
| WO | WO2015179329 | 11/2015 |
| WO | WO2015189354 | 12/2015 |
| WO | WO2015191646 | 12/2015 |
| WO | WO2016014955 | 1/2016 |
| WO | WO2017024258 | 2/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018049317 | 3/2018 |
| WO | WO2018065092 | 4/2018 |
| WO | WO2018080590 | 5/2018 |
| WO | WO2018148174 | 8/2018 |
| WO | WO2019010318 | 1/2019 |
| WO | WO2019050765 | 3/2019 |
| WO | WO2019075444 | 4/2019 |
| WO | WO2019094456 | 5/2019 |
| WO | WO2019173475 | 9/2019 |
| WO | WO2019222117 | 11/2019 |
| WO | WO2019246240 | 12/2019 |
| WO | WO2020036809 | 2/2020 |
| WO | WO2021067134 | 4/2021 |
| WO | WO2021076954 | 4/2021 |
| WO | WO2021127202 | 6/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |
| WO | WO2023137341 | 7/2023 |
| WO | WO2023147353 | 8/2023 |
| WO | WO2023154612 | 8/2023 |
| WO | WO2023192925 | 10/2023 |

OTHER PUBLICATIONS

Gibbs, et al., "Temporary Stent as a bail-out device during percutaneous transluminal coronary angioplasty: preliminary clinical experience," British Heart Journal, 1994, 71:372-377, Oct. 12, 1993 6 pgs.

Gupta, S. et al., "Acute Pulmonary Embolism Advances in Treatment", JAPI, Association of Physicians India, Mar. 2008, vol. 56, 185-191.

International Search Report and Written Opinion for International App. No. PCT/US13/61470, dated Jan. 17, 2014, 7 pages.

International Search Report and Written Opinion for International App. No. PCT/US2014/046567, dated Nov. 3, 2014, 13 pages.

International Search Report and Written Opinion for International App. No. PCT/US2014/061645, dated Jan. 23, 2015, 15 pages.

International Search Report for International App. No. PCT/US13/71101, dated Mar. 31, 2014, 4 pages.

Konstantinides, S. et al., "Pulmonary embolism hotline 2012—Recent and expected trials", Thrombosis and Haemostasis, Jan. 9, 2013:33; 43-50.

Konstantinides, S. et al., "Pulmonary embolism: risk assessment and management", European Society of Cardiology; European Heart Journal, Sep. 7, 2012:33, 3014-3022.

Kucher, N. et al., "Percutaneous Catheter Thrombectomy Device for Acute Pulmonary Embolism: In Vitro and in Vivo Testing", Circulation, Sep. 2005:112:e28-e32.

Kucher, N., "Catheter Interventions in Massive Pulmonary Embolism", Cardiology Rounds, Mar. 2006 vol. 10, Issue 3, 6 pages.

Kucher, N. et al., "Management of Massive Pulmonary Embolism", Radiology, Sep. 2005:236:3 852-858.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.

Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.

Lee, L. et al, "Massive pulmonary embolism: review of management strategies with a focus on catheter-based techniques", Expert Rev. Cardiovasc. Ther. 8(6), 863-873 (2010).

Liu, S. et al, "Massive Pulmonary Embolism: Treatment with the Rotarex Thrombectomy System", Cardiovascular Interventional Radiology; 2011: 34:106-113.

Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.

Reekers, J. et al., "Mechanical Thrombectomy for Early Treatment of Massive Pulmonary Embolism", CardioVascular and Interventional Radiology, 2003: 26:246-250.

Schmitz-Rode et al., "New Mesh Basket for Percutaneous Removal of Wall-Adherent Thrombi in Dialysis Shunts," Cardiovasc Intervent Radiol 16:7-10 1993 4 pgs.

Schmitz-Rode et al., "Temporary Pulmonary Stent Placement as Emergency Treatment of Pulmonary Embolism," Journal of the American College of Cardiology, vol. 48, No. 4, 2006 (5 pgs.).

Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.

Spiotta, A et al., "Evolution of thrombectomy approaches and devices for acute stroke: a technical review." J NeuroIntervent Surg 2015, 7, pp. 7 pages.

Svilaas, T. et al., "Thrombus Aspiration During Primary Percutaneous Coronary Intervention." The New England Journal of Medicine, 2008, vol. 358, No. 6, 11 pages.

Tapson, V., "Acute Pulmonary Embolism", The New England Journal of Medicine, Mar. 6, 2008:358:2037-52.

The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.

Truong et al., "Mechanical Thrombectomy of Iliocaval Thrombosis Using a Protective Expandable Sheath," Cardiovasc Intervent Radiol27-254-258, 2004, 5 pgs.

Turk et al., "ADAPT FAST study: a direct aspiration first pass technique for acute stroke thrombectomy." J NeuroIntervent Surg, vol. 6, 2014, 6 pages.

(56) References Cited

OTHER PUBLICATIONS

Uflacker, R., "Interventional Therapy for Pulmonary Embolism", Journal of Vascular and Interventional Radiology, Feb. 2001: 12:147-164.
Verma, R., MD et al. "Evaluation of a Newly Developed Percutaneous Thrombectomy Basket Device in Sheep With Central Pulmonary Embolisms", *Investigative Radiology*, Oct. 2006, 41, 729-734.
International Search Report and Written Opinion for International App. No. PCT/US2015/034987 filed Jun. 9, 2015, Applicant: Inceptus Medical, LLC, dated Sep. 17, 2015, 12 pages.
English translation of Japanese Office Action received for JP Application No. 2016-564210, Applicant: Inceptus Medical, LLC, dated Sep. 4, 2017, 4 pages.
Australian Exam Report received for AU Application No. 2015274704, Applicant: Inceptus Medical, LLC, dated Sep. 7, 2017, 3 pages.
European Search Report received for EP Application No. 15805810.7, Applicant: Inceptus Medical, LLC, dated Sep. 4, 2017, 6 pages.
International Search Report and Written Opinion for International App. No. PCT/US2016/067628 filed Dec. 19, 2016, Applicant: Inari Medical, Inc., dated Apr. 10, 2017, 11 pages.
Goldhaber, S. et al. "Percutaneous Mechanical Thrombectomy for Acute Pulmonary Embolism—A Double-Edged Sword," American College of CHEST Physicians, Aug. 2007, 132:2, 363-372.
Goldhaber, S., "Advanced treatment strategies for acute pulmonary embolism, including thrombolysis and embolectomy," Journal of Thrombosis and Haemostasis, 2009: 7 (Suppl. 1): 322-327.
International Search Report and Written Opinion for International App. No. PCT/US2017/029696, Date of Filing: Apr. 26, 2017, Applicant: Inari Medical, Inc., dated Sep. 15, 2017, 19 pages.
International Search Report and Written Opinion for International App. No. PCT/US2016/058536, Date of Filing: Oct. 24, 2016, Applicant: Inari Medical, Inc., dated Mar. 13, 2017, 14 pages.
European First Office Action received for EP Application No. 13838945.7, Applicant: Inari Medical, Inc., dated Oct. 26, 2018, 7 pages.
International Search Report and Written Opinion for International App. No. PCT/US2018/048786, Date of Filing: Aug. 30, 2018, Applicant: Inari Medical, Inc., dated Dec. 13, 2018, 12 pages.
International Search Report and Written Opinion for International App. No. PCT/US2018/055780, Date of Filing: Oct. 13, 2018, Applicant: Inceptus Medical LLC., dated Jan. 22, 2019, 8 pages.
European Search Report for European Application No. 16876941.2, Date of Filing: Dec. 19, 2016, Applicant: Inari Medical, Inc., dated Jul. 18, 2019, 7 pages.
Extended European Search Report for European Application No. 16858462.1, Date of Filing: Oct. 24, 2016, Applicant: Inari Medical, Inc., dated Jun. 3, 2019, 10 pages.
International Search Report and Written Opinion for International App. No. PCT/US2019/045794, Date of Filing: Aug. 8, 2019, Applicant: Inari Medical, Inc., dated Nov. 1, 2019, 17 pages.
Partial Supplementary European Search Report for European Application No. 17864818.4, Date of Filing: May 21, 2019, Applicant: Inari Medical, Inc., dated Apr. 24, 2020, 11 pages.
International Search Report and Written Opinion for International App. No. PCT/US2020/056067, Date of Filing: Oct. 16, 2020; Applicant: Inari Medical, Inc., dated Jan. 22, 2021, 8 pages.
Extended European Search Report for European Application No. 20191581.6, Applicant: Inari Medical, Inc., dated Mar. 31, 2021, 11 pages.
International Search Report and Written Opinion for International App. No. PCT/US2020/055645, Date of Filing: Dec. 17, 2020; Applicant: Inari Medical, Inc., dated Apr. 14, 2021, 12 pages.
Extended European Search Report for European Application No. 18853465.5, Applicant: Inari Medical, Inc., dated May 7, 2021, 2021, 7 pages.
Vorwerk, D. MD, et al., "Use of a Temporary Caval Filter to Assist Percutaneous Iliocaval Thrombectomy: Experimental Results." SCVIR, 1995, 4 pages.
PCT International Search Report and Written Opinion for International Appln. No. PCT/US2020/014854, dated Oct. 5, 2020 (13 pages).
PCT International Search Report and Written Opinion for International Appln. No. PCT/US2020/018655, dated Dec. 16, 2020 (22 pages).
PCT International Search Report and Written Opinion for International Appln. No. PCT/US2020/017684, dated Nov. 30, 2020 (19 pages).
Extended European Search Report for EP Patent Appln. No. 20185092.2 dated Sep. 11, 2020, 6 pages.
EP Examination Report for EP Patent Appln. No. 18745794.0 dated Jul. 20, 2020, 4 pages.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information);retrieved from the internet: http://www.bostonscientific.com/en-us/products/thrombectomy-systems/fetch2-aspiration-catheter.html; 2 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 7 pgs.; retrieved/printed: Mar. 24, 2016.
Youtube; Merci Retrieval System X Series Animation; uploaded Mar. 16, 2009 (product information); posted on May 7, 2009 by SSMDePAUL, time 1:09, retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.
PCT International Search Report and Written Opinion for International Patent Appln. No. PCT/US2019/050467, Applicant Stryker Corporation, dated Dec. 18, 2019 (17 pages).
PCT International Search Report and Written Opinion for International Appln. No. PCT/US2017/029440, Applicant Stryker Corporation, dated Jul. 7, 2017.
PCT International Search Report and Written Opinion for International Appln. No. PCT/US2017/029472, Applicant Stryker Corporation, dated Jul. 7, 2017.
PCT International Search Report and Written Opinion for International Appln. No. PCT/US2017/035543, Applicant Stryker Corporation, dated Aug. 14, 2017.
PCT International Search Report and Written Opinion for International Appln. No. PCT/US2017/029366, Applicant Stryker Corporation, dated Aug. 29, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
International search report and written opinion dated Feb. 28, 2018 for PCT/US2017/029345, Applicant Stryker Corporation 26 pages.
Extended European Search Report dated Aug. 22, 2018 for European patent appln No. 16852212.6, 6 pages.
Extended European Search Report dated Oct. 5, 2018 for European patent appln No. 18174891.4, 6 pages.
International search report and written opinion dated Nov. 14, 2018 for PCT/US2018/040937, Applicant Stryker Corporation 16 pages.
International Search Report and Written Opinion dated Mar. 28, 2019 for International Appln. No. PCT/US2018/059607.

(56) References Cited

OTHER PUBLICATIONS

International Search Report and Written Opinion dated May 6, 2016 for PCT/US2016/017982.

PCT International Search Report and Written Opinion for International Patent Appln. No. PCT/US2019/032601, Applicant Stryker Corporation, dated Jul. 23, 2019 (12 pages).

Extended European Search Report dated Oct. 8, 2019 for European Patent Application No. 19191925.7.

International Search Report and Written Opinion for International Patent Appln. No. PCT/US2019/050410 dated Oct. 25, 2019.

International Search Report and Written Opinion for International App. No. PCT/US21/35965, Date of Filing: Jun. 4, 2021, Applicant: Inari Medical, Inc., dated Sep. 28, 2021, 12 pages.

International Search Report and Written Opinion for International App. No. PCT/US21/45072 Date of Filing: Aug. 6, 2021, Applicant: Inari Medical, Inc., dated Jan. 20, 2022, 10 pages.

International Search Report and Written Opinion for International App. No. PCT/US21/58793; Date of Filing: Nov. 10, 2021, Applicant: Inari Medical, Inc., dated Mar. 16, 2022, 13 pages.

International Search Report and Written Opinion for International App. No. PCT/US21/59718; Date of Filing: Nov. 17, 2021, Applicant: Inari Medical, Inc., dated Mar. 22, 2022, 13 pages.

International Search Report and Written Opinion for International App. No. PCT/US21/59735; Date of Filing: Nov. 17, 2021, Applicant: Inari Medical, Inc., Date of Mailing: Mar. 22, 2022, 11 pages.

International Search Report and Written Opinion for International App. No. PCT/US23/60502; Date of Filing: Jan. 11, 2023, Applicant: Inari Medical, Inc., dated May 25, 2023, 9 pages.

International Search Report and Written Opinion for International App. No. PCT/US23/61256; Date of Filing: Jan. 25, 2023, Applicant: Inari Medical, Inc., dated Jun. 7, 2023, 8 pages.

Gross et al., "Dump the pump: manual aspiration thrombectomy (MAT) with a syringe is technically effective, expeditious, and cost-efficient," J NeuroIntervent Surg, 2018, 4 pages.

International Search Report and Written Opinion for International App. No. PCT/US23/60927; Date of Filing: Jan. 19, 2023, Applicant: Inari Medical, Inc., dated Jul. 20, 2023, 12 pages.

Extended European Search Report issued for EP Application No. 20877370.5, dated Oct. 17, 2023, 11 pages.

* cited by examiner

HEMOSTASIS VALVES AND METHODS OF USE

CROSS-REFERENCE TO RELATED APPLICATIONS

This application is a divisional of U.S. patent application Ser. No. 17/705,189, filed on Mar. 25, 2022, and titled "HEMOSTASIS VALVES AND METHODS OF USE," which is a continuation of U.S. patent application Ser. No. 17/226,318, filed on Apr. 9, 2021, and titled "HEMOSTASIS VALVES AND METHODS OF USE," which is a continuation of U.S. patent application Ser. No. 16/117,519, filed on Aug. 30, 2018, now issued as U.S. Pat. No. 11,000,682, and titled "HEMOSTASIS VALVES AND METHODS OF USE," which claims the benefit of U.S. Provisional Patent Application No. 62/554,931, filed on Sep. 6, 2017, and titled "HEMOSTASIS VALVES AND METHODS OF USE," each of which is herein incorporated by reference herein in its entirety.

BACKGROUND

During a surgical procedure, a portion of a patient's body (e.g., vasculature) is accessed to allow for performance of a desired intervention or treatment. During such surgical procedures, it is desired to minimize patient blood loss, prevent delivery of air into the vasculature, and to maintain the sterility of the accessed portions or sites of the patient's body so as to prevent issues such as infection. Further, the desire for improved patient outcomes has led to the development of hemostasis valves that facilitate minimally invasive surgery.

In minimally invasive surgery, small incisions are created through a blood vessel which one or several catheters are inserted. Each of these one or several catheters can define a lumen extending longitudinally through that catheter. These catheters are moved to a position proximate to tissue, nerves, or other body structures targeted by the surgery, and then tools for performing the procedure are inserted through the lumens of some or all of these catheters.

To minimize blood loss, prevent delivery of air into the vasculature, and to facilitate maintenance of sterility within the patient's body (e.g., blood vessel), these catheters are equipped with hemostasis valves. These valves seal or selectably seal the lumens of the catheters. In many instances, these valves can seal the lumen of the catheter when a tool extends through the catheter, and specifically through the valve. Additionally the valves can seal the lumen when a tool is removed or does not extend through the catheter.

While such traditional hemostasis valves are greatly beneficial for intravascular access, they have some drawbacks. For example, some valves may not seal adequately for all interventional applications or tools, and/or the operation of some valves may be complicated for operator use. The drawbacks of such valve designs may in turn increase the complexity of any surgery performed therewith and/or reduce patient safety (e.g., bleeding, infection, and/or other detrimental complications). Accordingly, new and improved hemostasis valves and methods of use are desired.

SUMMARY

The following relates to valves, medical systems incorporating valves, and methods of using the same. The valve can include a tubular member that can be constricted, collapsed, and/or sealed by one or several tensioning mechanisms. The tensioning mechanism can include at least one filament that extends around at least a portion of the tubular member. The filament can interact with the tubular member to constrict, collapse, and/or seal the tubular member via manipulation of the tensioning mechanism(s). A tool can be inserted through the valve to gain access to a patient's body and specifically to gain access to a blood vessel. Through the use of the tensioning mechanism and filament to constrict, collapse, and/or seal the tubular member, the valve can seal around a wide range of tool sizes and shapes, as well as multiple tools of differing sizes simultaneously. Additionally, such a valve creates a robust seal that maintains its seal when a vacuum is applied such as occurs during aspiration.

Aspects of the present disclosure relate to a hemostatic valve for sealing a medical device. The hemostatic valve includes an elongate member having a first end, a second end, and a central lumen extending therebetween. In some embodiments, the elongate member is pliable. The hemostatic valve can include a reinforcement structure extending along at least a portion of the elongate member, such that the reinforcement structure is coupled to the elongate member. The hemostatic valve includes an active tensioning mechanism coupled to the elongate member. In some embodiments, the tensioning mechanism is moveable between a first configuration in which the central lumen is constricted and sealed and a second configuration in which the central lumen is open. Optionally, the valve may be manually adjusted by the user to intermediate positions between fully open and fully closed. Additionally, an instrument (e.g. catheter) may provide an intermediate position where the valve creates hemostasis without user adjustment.

In some embodiments, the elongate member can be a compliant polymer tube. In some embodiments, the tensioning mechanism can include at least one filament extending at least partially around the elongate member. In some embodiments, the reinforcement structure is positioned between the at least one filament and the elongate member. In some embodiments, the reinforcement structure can be a braided mesh. In some embodiments, the reinforcement structure is coupled to the elongate member at a position proximate to the first end of the elongate member and at a position proximate to the second end of the elongate member. In some embodiments, the reinforcement structure is not coupled to the elongate member at a position between the first end of the elongate member and the second end of the elongate member. In some embodiments, the central portion of the compliant polymer tube that is constrained or collapsed by the tensioning mechanism, and at least one filament, is not coupled to the reinforcement structure.

In some embodiments, the tensioning mechanism can include an actuator coupled to the at least one filament. In some embodiments there are two tensioning mechanisms coupled to the at least one filament that operate in opposite directions. In some embodiments the two tensioning mechanisms are attached to the same filament. In some embodiments the two tensioning mechanisms are attached to opposing filaments. In some embodiments, the actuator can be moveable to control movement of the at least one filament from a first position in which the central lumen is constricted and sealed to a second position in which the central lumen is open. In some embodiments, the at least one filament is in the first position when the tensioning mechanism is in the first configuration. In some embodiments, the actuator is biased towards the first position. In some embodiments, the actuator is biased toward the second position. In some embodiments, the actuator can be a manual actuator.

In some embodiments, the at least one filament forms a loop around the elongate member. In some embodiments, the at least one filament forms a bight around a portion of the elongate member. In some embodiments, the at least one filament can include a first filament and a second filament. In some embodiments, each of the first filament and the second filament are coupled to the same actuator. In some embodiments, each of the first filament and the second filament are coupled to different actuators. In some embodiments, the first filament and the second filament are moveable from the first position to the second position. In some embodiments, each of the first filament and the second filament form a loop around the elongate member. In some embodiments, the first filament forms a first bight around a first portion of the elongate member, and the second filament forms a second bight around a second portion of the elongate member. In some embodiments, the first bight extends through the second bight.

In some embodiments, the hemostatic valve can include a shell defining a first aperture and a second aperture. In some embodiments, the elongate member extends from the first aperture to the second aperture and fluidly couples the first aperture and the second aperture. In some embodiments, the tensioning mechanism is self-adjustable to seal around tools of different sizes extending through the hemostatic valve. In some embodiments, the central lumen can comprise a single lumen, and in some embodiments, the central lumen can comprise a plurality of lumens.

One aspect of the present disclosure relates to a delivery system for intravascular access of a blood vessel within a patient's body. The delivery system includes a catheter having a first end, a second end, and a catheter lumen extending therebetween and a hemostatic valve coupled to the first end of the catheter. The hemostatic valve includes a tubular member having a first end, a second end, and a central lumen extending therebetween. In some embodiments, the central lumen of the tubular member is fluidly coupled with the catheter lumen. The hemostatic valve includes an active tensioning mechanism coupled to the tubular member, the tensioning mechanism can be moveable between a first configuration in which the tensioning mechanism constricts on the central lumen and the central lumen is sealed and a second configuration in which the central lumen is open.

In some embodiments, the hemostatic valve further includes a reinforcement structure extending along at least a portion of the tubular member. In some embodiments, the reinforcement structure is located between the tensioning mechanism and the tubular member. In some embodiments, the reinforcement structure can be a braided mesh. In some embodiments, the reinforcement structure is coupled to the tubular member at a position proximate to the first end of the tubular member and at a position proximate to the second end of the tubular member. In some embodiments, the reinforcement structure is adhered to the tubular member at the first end of the tubular member and at the second end of the tubular member. In some embodiments, the reinforcement structure is uncoupled to the tubular member between the first end of the tubular member and the second end of the tubular member.

In some embodiments, the tensioning mechanism can include at least one filament extending at least partially around the tubular member. In some embodiments, the tensioning mechanism can include an actuator coupled to the at least one filament. In some embodiments, moving the tensioning mechanism from the first configuration to the second configuration can include moving the actuator and the thereto coupled at least one filament from a first position to a second position. In some embodiments, the filament constricts and seals the central lumen of the tubular member when the filament is in the first position.

In some embodiments, the actuator can be a manual actuator. In some embodiments, the actuator can include a pair of opposing and depressable buttons, which buttons can be biased towards an undepressed position. In some embodiments, the central lumen is sealed when the buttons are in the undepressed position. In some embodiments, the filament can be a monofilament. In some embodiments, the filament can be at least one of: a polymer filament; or a metallic filament. In some embodiments, the catheter can include a thrombus extraction device.

One aspect of the present disclosure relates to a method of sealing a delivery device accessing a blood vessel of a patient. The method includes inserting the delivery device including a catheter and a hemostatic valve into the blood vessel of the patient. In some embodiments, the catheter can have a first end, a second end, and a catheter lumen extending therethrough. In some embodiments, the hemostatic valve can be coupled to the first end and can have a tubular member defining a central lumen fluidly coupled with the catheter lumen and a tensioning mechanism coupled with the tubular member. In some embodiments, the tensioning mechanism collapses and seals the central lumen in a first configuration and thereby seals access to the blood vessel. The method can include moving the tensioning mechanism of the hemostatic valve to a second configuration. In some embodiments, the central lumen is open and access to the blood vessel is unsealed when the tensioning mechanism is in the second configuration. The method can include advancing a shaft of a tool through the delivery device until a first end of the tool reaches a desired position within the blood vessel of the patient and a portion of the shaft is positioned within the central lumen of the tubular member. The method can include returning the tensioning mechanism of the hemostatic valve to the first configuration such that the tubular member collapses on the shaft of the tool and seals around the shaft of the tool.

In some embodiments, the method includes retracting the shaft of the tool from the delivery device. In some embodiments, the tensioning mechanism is maintained in the first configuration during and after the retracting of the shaft of the tool from the delivery device. In some embodiments, the tensioning mechanism is moved to the second configuration during the retracting of the shaft of the tool from the delivery device, and the tensioning mechanism is returned to the first configuration after the shaft of the tool is retracted from the delivery device.

In some embodiments, the tensioning mechanism can include at least one filament extending at least partially around the tubular member. In some embodiments, the at least one filament collapses the tubular member when the tensioning mechanism is in the first configuration. In some embodiments, the at least one filament circumferentially constricts the tubular member to collapse the tubular member when the tensioning mechanism is in the first configuration. In some embodiments, the hemostatic valve can include a reinforcement structure located between the at least one filament and the tubular member.

In some embodiments, the at least one filament forms a loop around the elongate member, and moving the tensioning mechanism from the second configuration to the first configuration reduces a size of the loop to thereby constrict the tubular member within the loop. In some embodiments, the filament forms at least one bight around a portion of the elongate member. In some embodiments, the filament can include a first filament and a second filament. In some embodiments, the at least one bight can include a first bight oriented in a first direction and formed by the first filament and a second bight oriented in a second direction and formed by the second filament. In some embodiments, the first and second bights overlap to encircle a portion of the tubular member within a constricting area.

In some embodiments, moving the tensioning mechanism from the second configuration to the first configuration can include moving the first bight in the first direction and the second bight in the direction to reduce the size of the constricting area and collapse and seal the central lumen of the tubular member. In some embodiments, the tensioning mechanism can include an actuator. In some embodiments, moving the tensioning mechanism to the second configuration can include manipulating the actuator. In some embodiments, the method includes applying a vacuum to the delivery device and/or delivery system to aspirate material through the catheter. In some embodiments, the central lumen remains sealed during the aspiration. In some embodiments, the tool can include a thrombus extraction device.

DETAILED DESCRIPTION

The present disclosure relates to a valve that can be used a hemostasis valve. This valve, also referred to herein as a garrote valve can seal with or without a tool extending through the valve. The garrote valve provides convenient, single-handed operation for a wide range of medical devices including catheters, wires, embolectomy systems, or the like. This single-handed operation of the garrote valve allows the user to easily and quickly swap different tools being used through the valve without compromising hemostasis and therefore simplifying the procedure. Combined with single-handed operation, the garrote valve provides robust sealing either with or without a tool extending through the valve. This robust sealing minimizes leakage in applications with a pressure differential on different sides of the valve. This pressure differential can arise, for example, during the application of vacuum aspiration in a procedure. Even under such conditions, as well as under other conditions, the garrote valve maintains seal integrity and prevents leakage in one or both directions.

The garrote valve includes a tubular member. The tubular member is a flexible member that defines a central lumen, which can, in some embodiments, define a single lumen, and in some embodiments, defines a plurality of lumens. In some embodiments, each of the plurality of lumens can comprise the same size and shape, and in some embodiments, some or all of the plurality of lumens can comprise different sizes and shapes. In some embodiments, for example, the plurality of lumens can comprise a lumen sized and/or shaped to receive a guide wire and a lumen sized and/or shaped to receive a tool. The tubular member extends at least partially through a constricting mechanism. The constricting mechanism can be moved from a first configuration to a second configuration, and the constricting mechanism can collapse and/or seal the central lumen of the tubular member when the constricting mechanism is in the first configuration. The constricting mechanism creates the above-discussed robust seal of the tubular member and thus of the valve.

Figure 1:
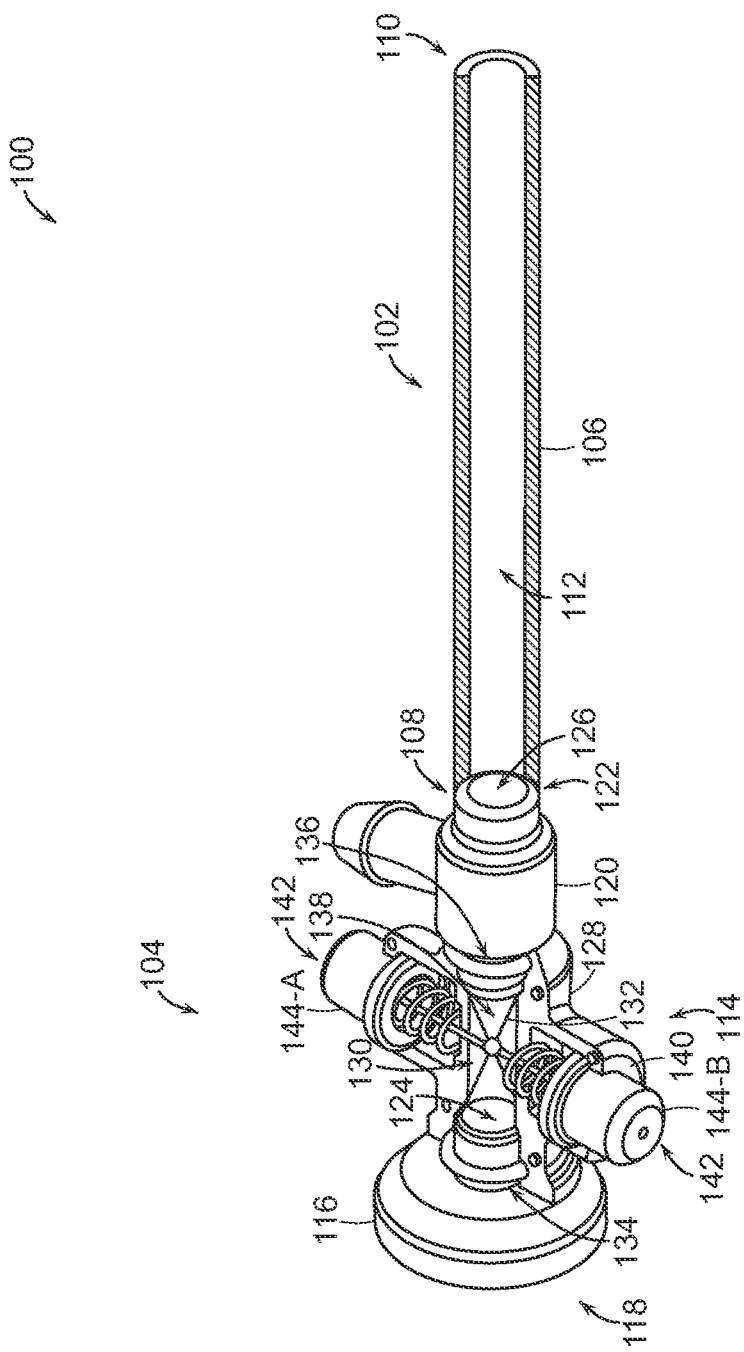
FIG. 1 is a perspective view of one embodiment of a delivery device.

With reference now to FIG. 1, a perspective view of one embodiment of a delivery system 100, also referred to herein as a delivery device 100, is shown. The delivery system 100 can include a catheter 102 and a garrote valve 104, also referred to herein as valve 104. The catheter 102 can comprise a shaft 106, also referred to herein as an elongate sheath 106, having a proximal end 108, also referred to herein as a first end 108, that can connect to the valve 104 and a distal end 110, also referred to herein as a second end 110. The shaft 106 can define a catheter lumen 112 extending from the proximal end 108 of the shaft 106 to the distal end 110 of the shaft 106. The catheter 102 and specifically the shaft 106 can comprise a variety of shapes and sizes and can be made from a variety of materials. In some embodiments, the catheter 102 can be flexible and/or can be made from a biocompatible material. The elongate sheath 106 can have an outer diameter of at least 4 French, at least 6 French, at least 8 French, at least 10 French, at least 12 French, at least 14 French, at least 18 French, at least 20 French, at least 22 French, between 4 French and 30 French, between 8 French and 24 French, between 12 French and 20 French, and/or any other or intermediate size.

The valve 104 can include an outer shell 114. The outer shell 114 can comprise a variety of shapes and sizes and can be made from a variety of materials. In some embodiments, the outer shell 114 can be made from one or several polymers or composites. The outer shell 114 can include features that allow interaction with and/or control of the valve 104 to move the valve 104 between the first configuration and the second configuration.

The outer shell 114 can include a proximal cap 116 located at a proximal end 118 of the outer shell 114 and a distal cap 120 located at a distal end 122 of the shell 114. The proximal cap 116 can include and/or house a proximal aperture 124, also referred to herein as a proximal channel 124, a first channel 124, or a first aperture 124, that extends through the proximal cap 116, and the distal cap 120 can include and/or house a distal aperture 126, also referred to herein as a distal channel 126, a second channel 126, or second aperture 126, that extends through the distal cap 120. As seen in FIG. 1, the distal cap 120 connects to the shaft 106 of the catheter 102 at the distal end 122 of the valve 104.

The proximal cap 116 and the distal cap 120 are connected via a housing 128. The housing 128 can be a one-piece housing 128 or a multi-piece housing 128. In the embodiment depicted in FIG. 1, the housing comprises a two-piece housing 128. The housing 128 can be configured to receive and couple with each of the proximal cap 116 and the distal cap 120, and as seen in FIG. 1, the housing 128 is coupled with each of the proximal cap 116 and the distal cap 120 to secure the relative position of the proximal cap 116 and the distal cap 120 with respect to each other.

The housing 128 can define an interior channel 130 through which an elongate member 132, also referred to herein as a tubular member 132, a septum 132, or a tubular septum 132, can extend and connect the proximal cap 116 and the distal cap 120. The elongate member 132 can comprise a variety of shapes and sizes and can be made from a variety of materials. In some embodiments, the elongate member 132 can comprise a compliant tubular structure that can be, for example, a thin-walled compliant tubular structure. The thin-walled structure of the elongate member 132 can facilitate the collapse, and specifically the uniform collapse of the elongate member 132 and the sealing of the elongate member 132. In some embodiments, the elongate member 132 is an elastic, resilient material that may comprise a polymer including either a natural or synthetic polymer. In some embodiments, the elongate member can comprise an elastic, resilient material that may comprise silicone, urethane, ethylene-vinyl acetate, natural or synthetic rubber or other elastomers known in the art. In some embodiments, the elongate member 132 can comprise a silicone tube.

Figure 2:
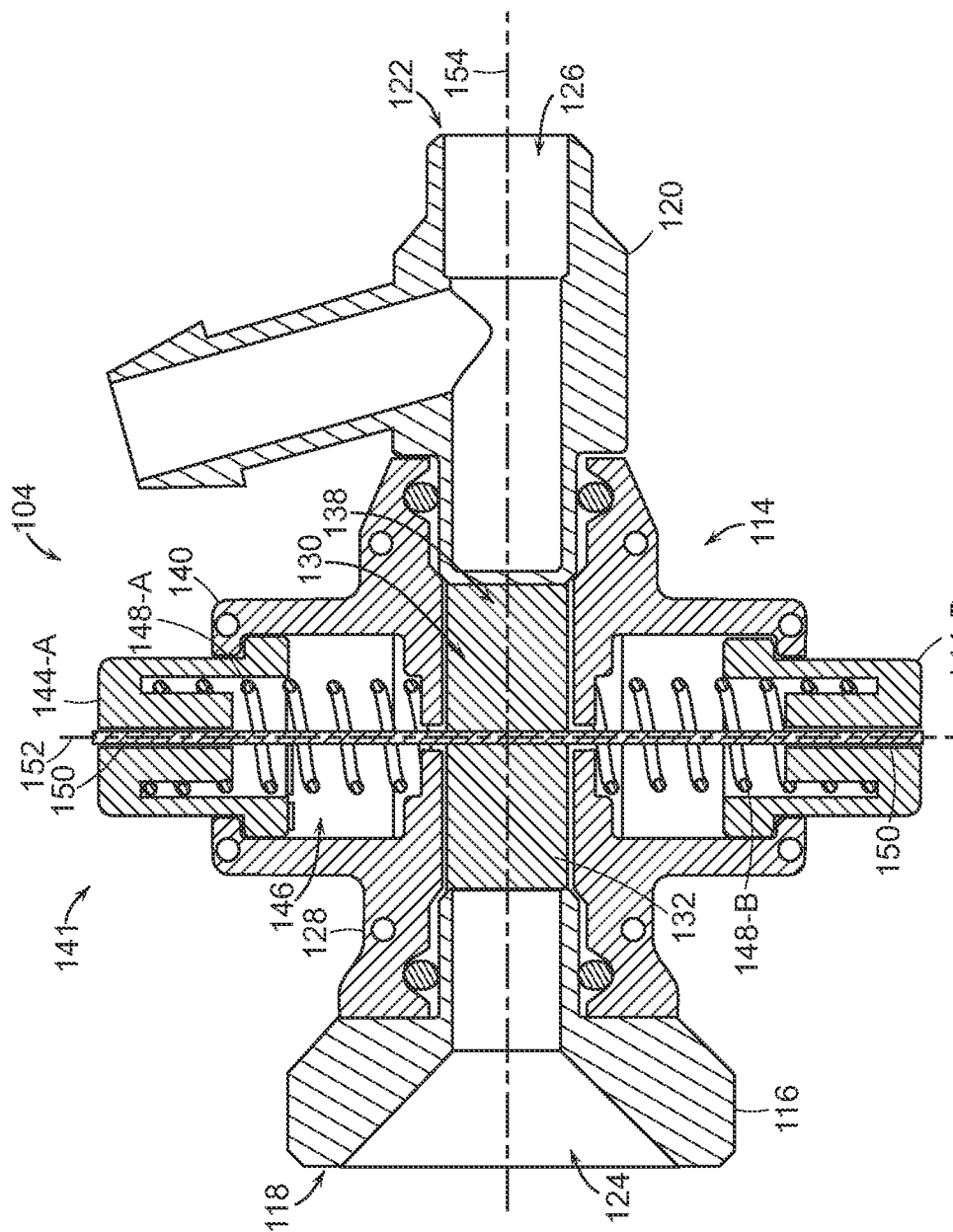
FIG. 2 is a side-section view of one embodiment of a hemostasis valve in a first configuration.
Figure 3:
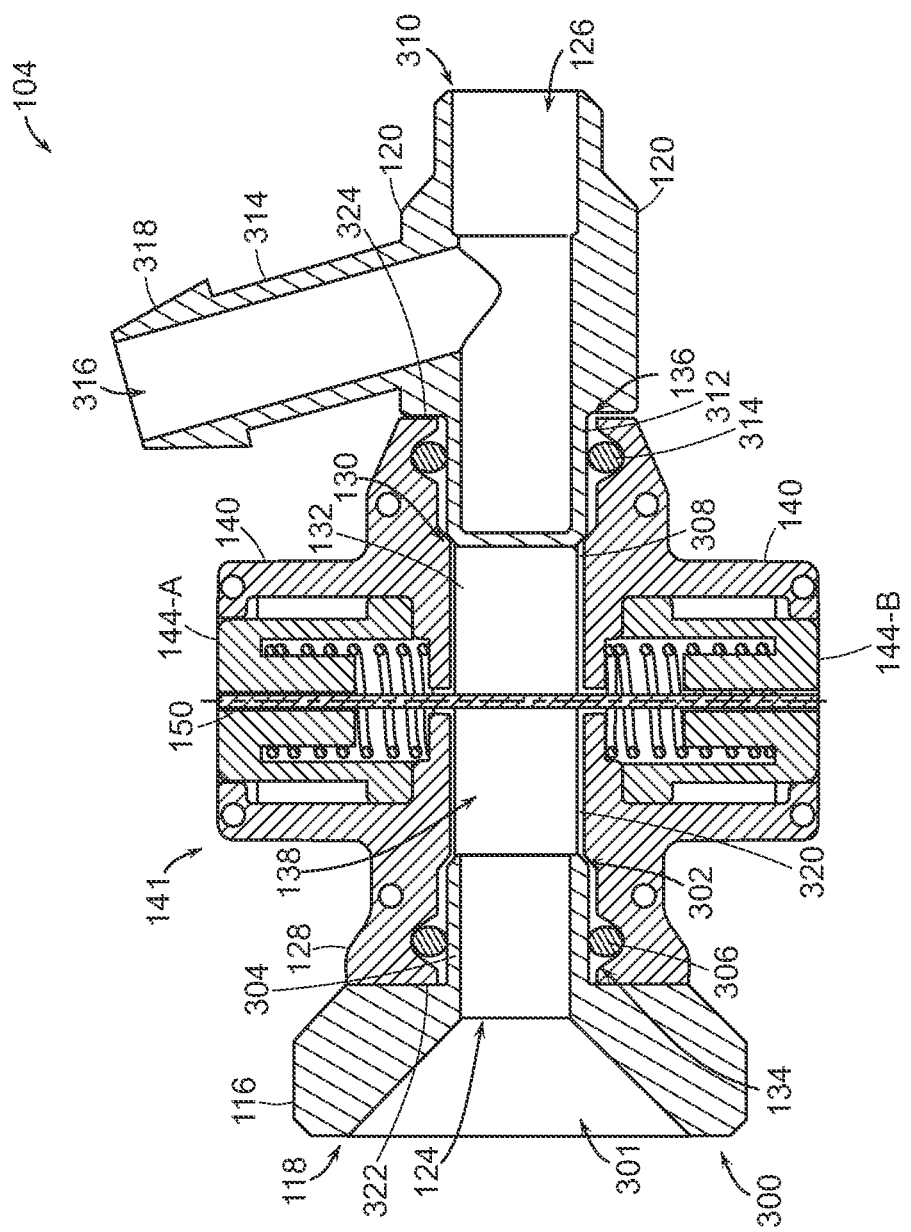
FIG. 3 is a side-section view of one embodiment of the valve in a second configuration.

The elongate member 132 can comprise a proximal end 134, also referred to herein as a first end 134, that can couple to the proximal cap 116, and a distal end 136, also referred to herein as a second end 136, that can couple to the distal cap 120. The elongate member 132 can define a central lumen 138 that can extend from the first end 134 to the second end 136 of the elongate member 132. The elongate member 132 can be coupled to the proximal cap 116 such that the central lumen 138 is fluidly coupled with the proximal aperture 124 of the proximal cap 116, and the elongate member 132 can be coupled to the distal cap 120 such that the central lumen 138, as seen in FIG. 2 and in FIG. 3, is fluidly coupled with the distal aperture 126 of the distal cap 120.

The central lumen 138 of the elongate member 132 can be defined by a wall of the elongate member 132 that can have a thickness that is uniform along the length of the elongate member 132 between the first end 134 and the second end 136, or that is non-uniform along the length of the elongate member 132 between the first end 134 and the second end 136. In some embodiments, the wall can have a thickness that is approximately between 0.005 inches and 0.05 inches, and/or approximately between 0.010 inches and 0.030 inches. As used anywhere herein, "approximately" refers to a range of +/−10% of the value and/or range of values for which "approximately" is used.

In some embodiments, the elongate member 132 can be cylindrically shaped, and specifically can be circular-cylindrically shaped. In some embodiments, the elongate member 132 can be dog-bone shaped to facilitate, for example, connection to each of the proximal cap 116 and the distal cap 120. In some embodiments, the elongate member 132 can include one or several outward-extending protuberances that engage with all or portions of a constricting mechanism 141, also referred to herein as a tensioning mechanism 141, of the valve 104 to secure a position of all or portions of the constricting mechanism 141 with respect to the elongate member 132. In some embodiments, the constricting mechanism 141 can be self-adjusting to seal around tools of different sizes extending through the valve 104.

The constricting mechanism 141 can, in some embodiments, collapse and seal the elongate member 132 via compression and/or constriction, and specifically via constriction with at least one filament 150. The constricting mechanism 141 can comprise: an actuator 142 which can be a manual actuator such as one or several buttons 144; and the at least one filament 150 that can extend at least partially around the elongate member 132. In some embodiments, the use of the constricting mechanism 141 can facilitate sealing of the valve around tools or instruments of a wide range of sizes and/or diameters, and particularly around tools or instruments that fit through the elongate member 132.

Figure 5:
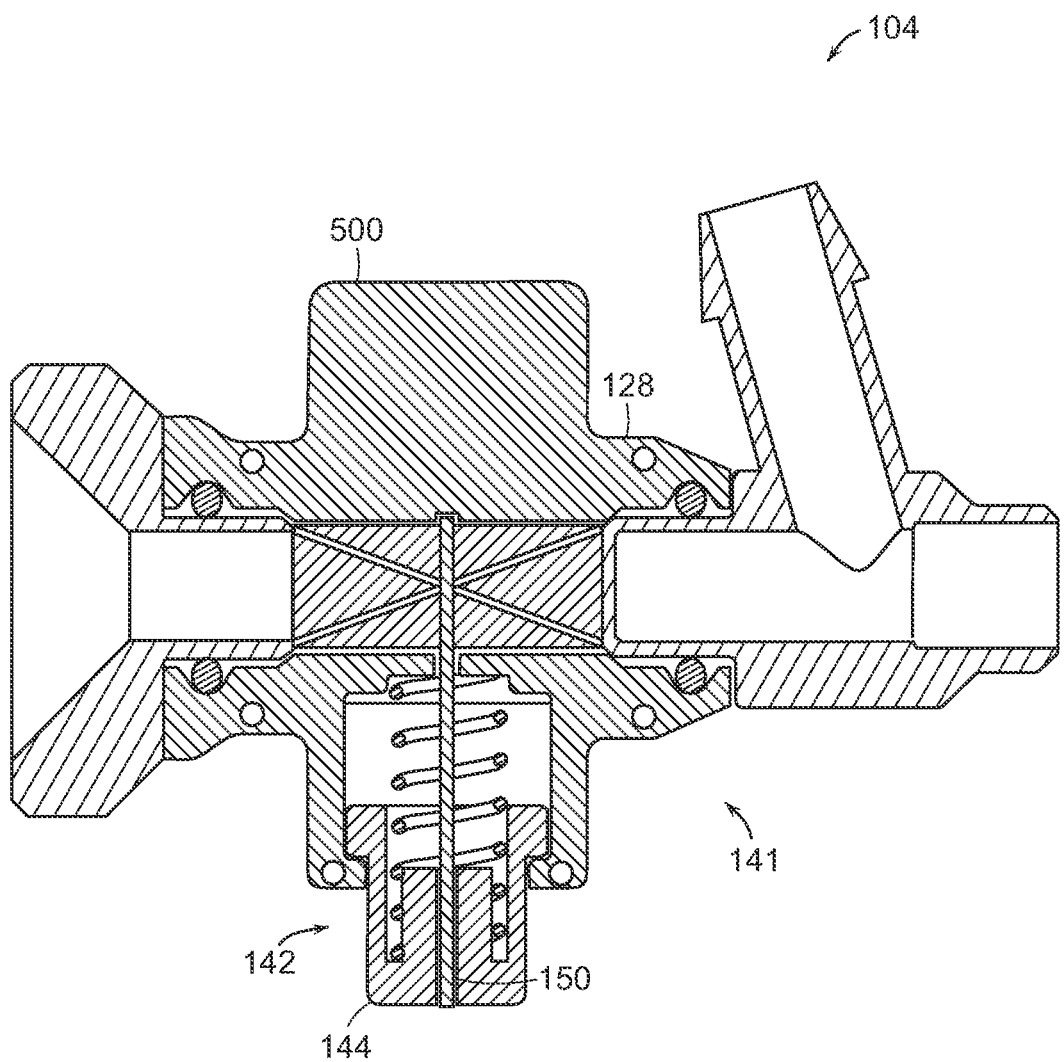
FIG. 5 is a side-section view of one embodiment of a single-button hemostasis valve in a first configuration.

The housing 128 can further include one or several retention features 140. The one or several retention features 140 of the housing can engage with and retain all or portions of the constricting mechanism 141 of the valve 104. In some embodiments, the one or several retention features 140 of the housing 128 can retain the actuator 142 and/or can couple the actuator 142 to the housing 128. The actuator 142 can comprise any desired type of actuator including, for example, a manual actuator and/or an automated actuator such as, for example, an electromechanical actuator including a solenoid-based actuator. In some embodiments, the actuator can comprise one or several buttons 144, and specifically, as depicted in FIG. 1, the actuator 142 can comprise a first button 144-A and a second button 144-B. Alternatively, and as depicted in FIG. 5, the actuator 142 can comprise a single button 144. In such an embodiment, the filament 150 can be coupled to the single button 144 and to a portion of the housing 128 such as, for example, to grip portion 500 of the housing 128 such that the movement of the single button 144 causes the sealing and/or opening of the elongate member 132 and of the valve 104.

The actuator 142 can be biased towards a configuration such as, for example, biased towards the first configuration or biased towards the second configuration. As depicted in FIG. 2, which shows the constricting mechanism 141 in the first configuration, the actuator 142 can be biased towards the first configuration wherein the elongate member 132 is collapsed and/or sealed by a bias feature 146. In this first configuration, the buttons 144 can be in a first position, also referred to herein as an undepressed position. This bias feature 146 can, as shown in FIG. 2, include a first spring 148-A configured to bias the first button 144-A towards the first position corresponding to the first configuration of the constricting mechanism 141, and a second spring 148-B configured to bias the second button 144-B towards a first position corresponding to the first configuration of the constricting mechanism 141. One or both of the first spring 148-A and the second spring 148-B can comprise a tension spring, compression spring, a torsion spring, a coil spring, or any other desired type of spring.

In some embodiments, one or both of the first spring 148-A and the second spring 148-B can generate sufficient force so as to allow actuation of the actuator 142 with a single hand and so as to collapse and seal the elongate member 132 when the constricting mechanism 141 is in the first configuration. In some embodiments, one or both of the first spring 148-A and the second spring 148-B can generate a force of: at least 0.1 pounds, at least 0.2 pounds, at least 0.3 pounds, at least 0.4 pounds, at least 0.5 pounds, at least 0.6 pounds, at least 0.7 pounds, at least 0.8 pounds, at least 0.9 pounds, at least 1 pound, at least 1.5 pounds, at least 2 pounds, at least 3 pounds, at least 5 pounds, and/or at least 10 pounds and in some embodiments one or both of the first spring 148-A and the second spring 148-B can generate a force approximately between: 0.1 and 10 pounds, 0.1 and 5 pounds, 0.1 and 1.5 pounds, 0.2 and 1 pounds, and/or 0.4 and 0.8 pounds.

The constricting mechanism 141 can include at least one filament 150 that extends at least partially around the elongate member 132. In some embodiments, the at least one filament 150 can circumferentially constrict the elongate member 132 to collapse and seal the elongate member 132 when the constricting mechanism 141 is in the first configuration. The filament can be made from a variety of materials including, for example, a polymer, a synthetic, and/or a metal. In some embodiments, the filament 150 can be nylon, stainless steel, nitinol, silicone, or the like. In some embodiments, the filament can comprise a single strand such as, for example, a monofilament, and in some embodiments, the filament can comprise a plurality of strands that can be, for example, twisted, woven, grouped, and/or fused to form the filament. In some embodiments, the filament 150 can comprise one or several threads, lines, cords, rope, ribbon, flat wire, sheet, or tape.

The filament 150 can be coupled to the actuator 142 such that the filament 150 selectively constricts, collapses, and/or seals the elongate member 132, and specifically the central lumen 138 of the elongate member 132 based on the movement and/or position of the actuator 142. In some embodiments, the filament 150 can be connected to one or both of the buttons 144-A, 144-B such that the filament 150 collapses, constricts, and/or seals the elongate member 132 and specifically the central lumen 138 of the elongate member 132 when the buttons 144-A, 144-B are in the first position, and the filament 150 can be connected to one or both of the buttons 144-A, 144-B such that the elongate member 132 and specifically the central lumen 138 of the elongate member 132 is open and uncollapsed when the buttons 144-A, 144-B are in the second position. In some embodiments in which the actuator 142 comprises a single button 144, as depicted in FIG. 5, the filament 150 can be connected to the button 144 and to the housing 128 such that the filament 150 is tightened when the button 144 moves to the first position.

In some embodiments, the at least one filament 150 can extend along an axis 152 that can be perpendicular to a central axis 154 of the elongate member 132 and/or of the apertures 124, 126. In some embodiments, the axis 152 of the at least one filament 150 can intersect and be perpendicular to the central axis 154 of the elongate member 132 and/or of the apertures 124, 126. In some embodiments, the actuator 142, and specifically the buttons 144-A, 144-B can move along this axis 152 when moved from the first position to the second position.

In FIG. 3, an embodiment of the valve 104 with the constricting mechanism 141 in the second configuration is shown. As specifically shown, both of the first and second buttons 144-A, 144-B are in the second position, depressed into the retention features 140 of the housing 128. In this second position, the filament 150 is loosened, thereby allowing the expansion of the elongate member 132 and the unsealing of the central lumen 138 of the elongate member 132.

As further seen in FIG. 3, the proximal cap 116 has a proximal end 300 and a distal end 302. The proximal cap 116 can include a funnel portion 301 of the proximal aperture 124, which funnel portion 301 can facilitate insertion of a tool into the proximal aperture 124. The distal end 302 of the proximal cap 116 can partially extend into the interior channel 130 of the housing 128. The proximal cap 116 can include a mating feature 304 that can mate with the proximal end 134 of the elongate member 132. In some embodiments, the proximal end 134 of the elongate member 132 can fit over the mating feature 304 of the proximal cap 116. The proximal end 134 of the elongate member 132 can be compressed between the mating feature 304 of the elongate member 132 and a portion of the interior channel 130 of the housing 128 into which the mating feature 304 is inserted to thereby secure the proximal end 134 of the elongate member 132 on the mating feature 304. In some embodiments, the proximal end 134 of the elongate member 132 can be further secured on the mating feature 304 by a proximal O-ring 306 that can be compressed between the housing 128 and the mating feature 304 of the proximal cap 116 to sealingly couple the elongate member 132 to the proximal cap 116.

The distal cap 120 has a proximal end 308 and a distal end 310. The distal cap can include a mating feature 312 located on the proximal end 308 of the distal cap 120, which mating feature 312 can mate with the distal end 136 of the elongate member 132. In some embodiments, the distal end 136 of the elongate member 132 can fit over the mating feature 312 of the distal cap 123. The distal end 136 of the elongate member 132 can be compressed between the mating feature 312 of the elongate member 132 and a portion of the interior channel 130 of the housing 128 into which the mating feature 312 is inserted to thereby secure the distal end 136 of the elongate member 132 on the mating feature 312. In some embodiments, the distal end 136 of the elongate member 132 can be further secured on the mating feature 312 by a distal O-ring 314 that can be compressed between the housing 128 and the mating feature 312 of the proximal cap 116 to sealingly couple the elongate member 132 to the distal cap 120.

The distal cap 120 can, in some embodiments, further include a side port barb 314 that can extend laterally away from the distal cap 120 and specifically away from the distal aperture 126 of the distal cap 120. The side port barb 314 can define a side port channel 316 that can extend through the side port barb 314 and fluidly connect to the distal aperture 126. In some embodiments, the side port barb 314 can include a securement feature 318 such as a barb that can secure coupling of a hose or tube to the side port barb 314.

In some embodiments, the side barb 314 can be used to apply a vacuum to the portions of the delivery device 100, and particularly to portions of the delivery device 100 that are distal of the axis 152 along which the elongate member 132 seals. This vacuum can be applied to aspirate a material through the delivery device 100, and specifically through the catheter 102 of the delivery device. This aspirated material can be a biological material including, for example, bodily fluids, multi-phase bodily materials that can include, for example, a fluidic portion and at least one solid portion, or the like.

In some embodiments, due to the narrowing shape of the elongate member 132 when the constricting mechanism 141 is in the first configuration, a vacuum applied to the portions of the delivery device 100 distal to the axis 152 draws the elongate member 132 towards the first configuration and can, in some embodiments, increase the strength, robustness, and/or strength of the seal of the valve 104. This attribute of the valve 104 can provide benefits over other valve designs in which a vacuum can compromise the seal of the valve, and thus the ability to draw a vacuum and aspirate can be limited.

In some embodiments, the valve 104 can further include a reinforcement structure 320 that can extend along all or portions of the elongate member 132. The reinforcement structure 320 can facilitate the uniform collapse of the elongate member 132, can prevent the at least one filament 150 from cutting through and/or tearing the elongate member 132, and can assist in guiding one or several tools through the elongate member 132. The reinforcement structure 320 can be tubular, can extend along and around the elongate member 132, and can be positioned so as to be between the elongate member 132 and the at least one filament 150.

The reinforcement structure 320 can include a proximal end 322 and a distal end 324. In some embodiments, the reinforcement structure 320 extends along and around the elongate member 132, and is positioned such that the proximal end 322 of the reinforcement structure 320 is proximate to the first end 134 of the elongate member 132 and the distal end 324 of the reinforcement structure 320 is proximate to the second end 136 of the elongate member 132.

The reinforcement structure 320 can be coupled to the elongate member 132. In some embodiments, the reinforcement structure 320 is coupled to the elongate member 132 along the length of the reinforcement structure 320, and in some embodiments, the reinforcement structure 320 is coupled to the elongate member 132 and distinct positions along the length of the elongate member 132 and/or the reinforcement structure 320. In one embodiment, for example, the reinforcement structure 320 can be coupled to the elongate member 132 at one or both of the proximal end 322 of the reinforcement structure 320 and the distal end 324 of the reinforcement structure 320 and/or at one or both of the first end 134 and the second end 136 of the elongate member 132. In some embodiments, the reinforcement structure 320 can be coupled to the elongate member 132 via one or several other components of the valve 104. In some embodiments, the reinforcement structure 320 can be coupled to the elongate member 132 via the compression of the reinforcement structure 320 and the elongate member 132 between the housing 128 and one or both of the proximal 116 and the distal 120.

In some embodiments, the reinforcement structure 320 can be adhered to the elongate member 132 via, for example, an adhesive such as silicone adhesive. In some embodiments, the adhesive can be circumferentially applied to the reinforcement structure 320 and/or the elongate member 132 in an adhesive ring that can, for example, a have a length approximately between: 0.010 inches and 0.5 inches; 0.02 and 0.4 inches; 0.050 inches and 0.0250 inches, or any other or intermediate range.

In one embodiment, each of the proximal end 322 and the distal end 324 of the reinforcement structure 320 can be adhered via an adhesive to the elongate member 132. In such an embodiment, the reinforcement structure 320 may be uncoupled to the elongate member 132 at positions other than the coupling at one or both of the proximal end 322 and the distal end 324 of the reinforcement structure 320, and thus the reinforcement structure 320 is uncoupled to the elongate member 132 at a position between the first end 134 and the second end 136 of the elongate member 134 and/or between the proximal end 322 and the distal end 324 of the reinforcement structure 320.

Figure 4:
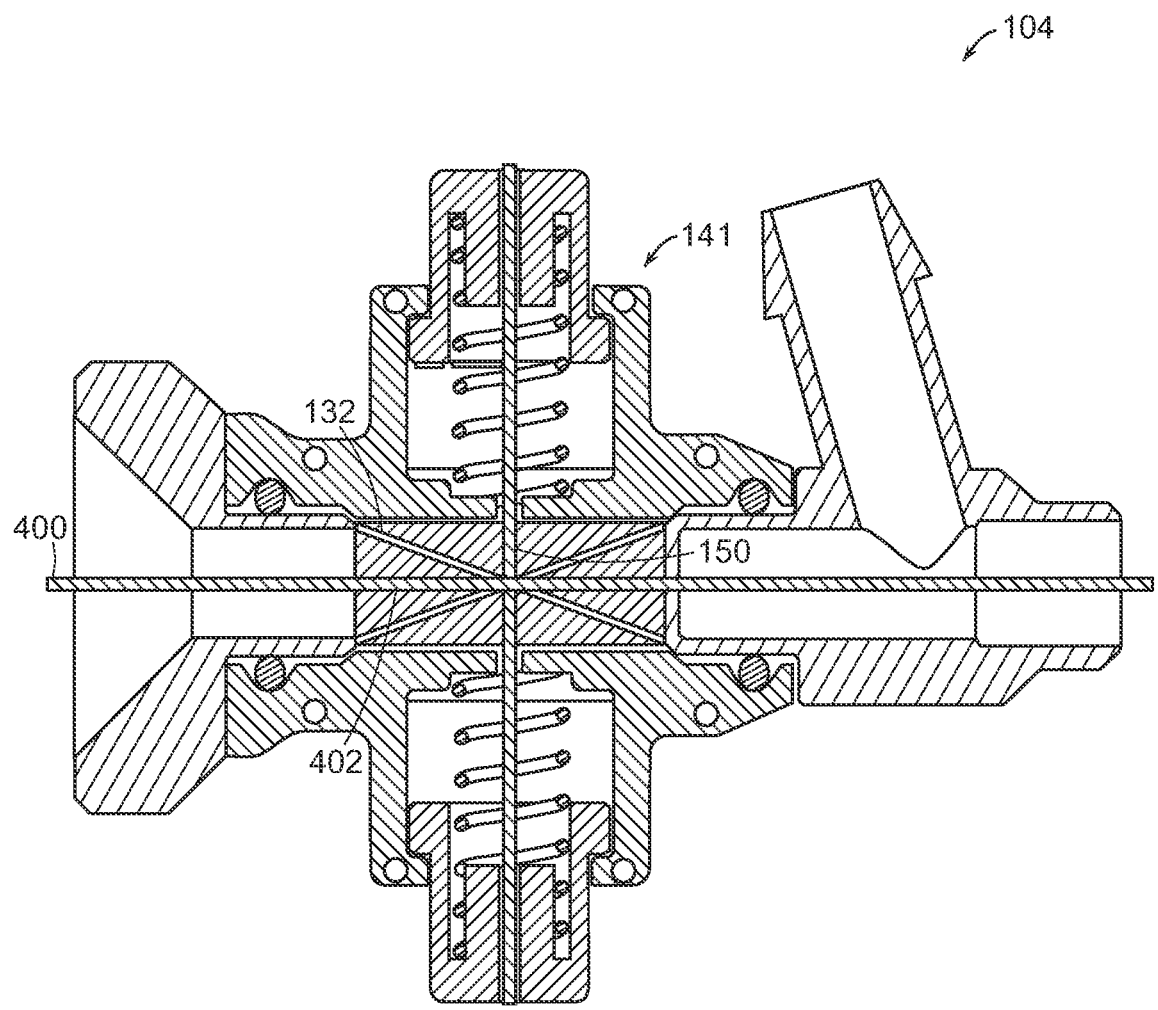
FIG. 4 is a side-section view of one embodiment of the valve in the first configuration and with a tool extending through the valve.

The lack of coupling of the reinforcement structure 320 to the elongate member 132 can facilitate and improve the collapse of the elongate member 132 around a tool 400, also referred to herein as instrument 400 or device 400, inserted through the valve 104 as shown in FIG. 4. The tool 400 can be any device inserted through the valve 104 including, for example, one or several additional catheters, lines, wires, grippers, punches, cutters, or the like. As seen in FIG. 4, the tool 400 is inserted through the valve 104 and specifically through the elongate member 132 of the valve. As shown, the constricting mechanism 141 is in the first configuration and the elongate member 132 and the central lumen 138 of the elongate member 132 is collapsed around the tool 400, and specifically around a shaft 402 of the tool 400 to thereby seal the valve 104 around the tool 400 and specifically around the shaft 402 of the tool 400. The constricting mechanism 141 can seal around tools 400 that fit through the elongate member 132, regardless of the size of the tool 400. Thus, the valve can be used with a wide variety of tools.

The reinforcement structure 320 can comprise a variety of designs, shapes, sizes, and materials. In some embodiments, the reinforcement structure 320 can be sized and shaped so as to receive elongate member 132 and to be positioned between the elongate member 132 and the at least one filament 150. In some embodiments, the reinforcement structure 320 can be made from a material sufficiently strong to prevent the cutting of the at least one filament 150 through the elongate member 132.

In some embodiments, the reinforcement structure can comprise a coil or a mesh sheath. The mesh sheath can, in some embodiments, comprise a braided mesh. The braided mesh can be made from any desired number of wires in any desired configuration. In some embodiments, the braided mesh can comprise a 4 wire braided mesh, an 8 wire braided mesh, a 12 wire braided mesh, a 16 wire braided mesh, a 20 wire braided mesh, a 24 wire braided mesh, a 32 wire braided mesh, a 48 wire braided mesh, a 64 wire braided mesh, a 72 wire braided mesh, an 80 wire braided mesh, a 96 wire braided mesh, or any other or intermediate braided mesh. In some embodiments, the braided mesh can comprise: a 1×1 configuration. In some embodiments, the wire in the braided mesh can be any desired material including, for example, a metal wire such as a nitinol wire or a stainless steel wire, a polymer wire, or a natural wire. In one embodiment, the braided mesh can comprise a 48 wire mesh in a 1×1 configuration made with a nitinol wire having a diameter of 0.003 inches.

Figure 6:
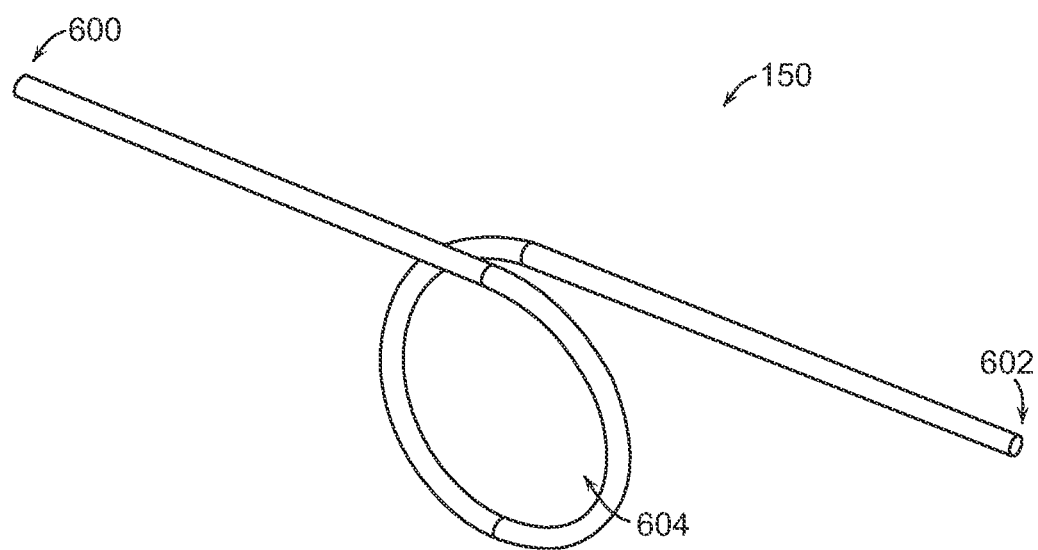
FIG. 6 is a perspective view of a filament of a valve forming a loop.

With reference now to FIGS. 6 through 9, different embodiments and/or configurations of the filament 150 are shown. The filament 150 can comprise a single filament 150 having a first end 600 and a second end 602 as shown in FIG. 6. The filament 150, and specifically which first and second ends 600, 602 can be coupled to the actuator 142 to move the filament 150 between the first and second configurations or positions and/or from the first configuration or position to the second configuration or position. In some embodiments, both of the first end 600 and the second end 602 can be coupled to a single button 144, in some embodiments, each of the first end 600 and the second end 602 can be coupled to different buttons 144, and in some embodiments, one of the first end 600 and the second end 602 can be coupled to a button 144 and the other of the first end 600 and the second end 602 can be coupled to the housing 128 or other portion of the valve 104.

Figure 7:
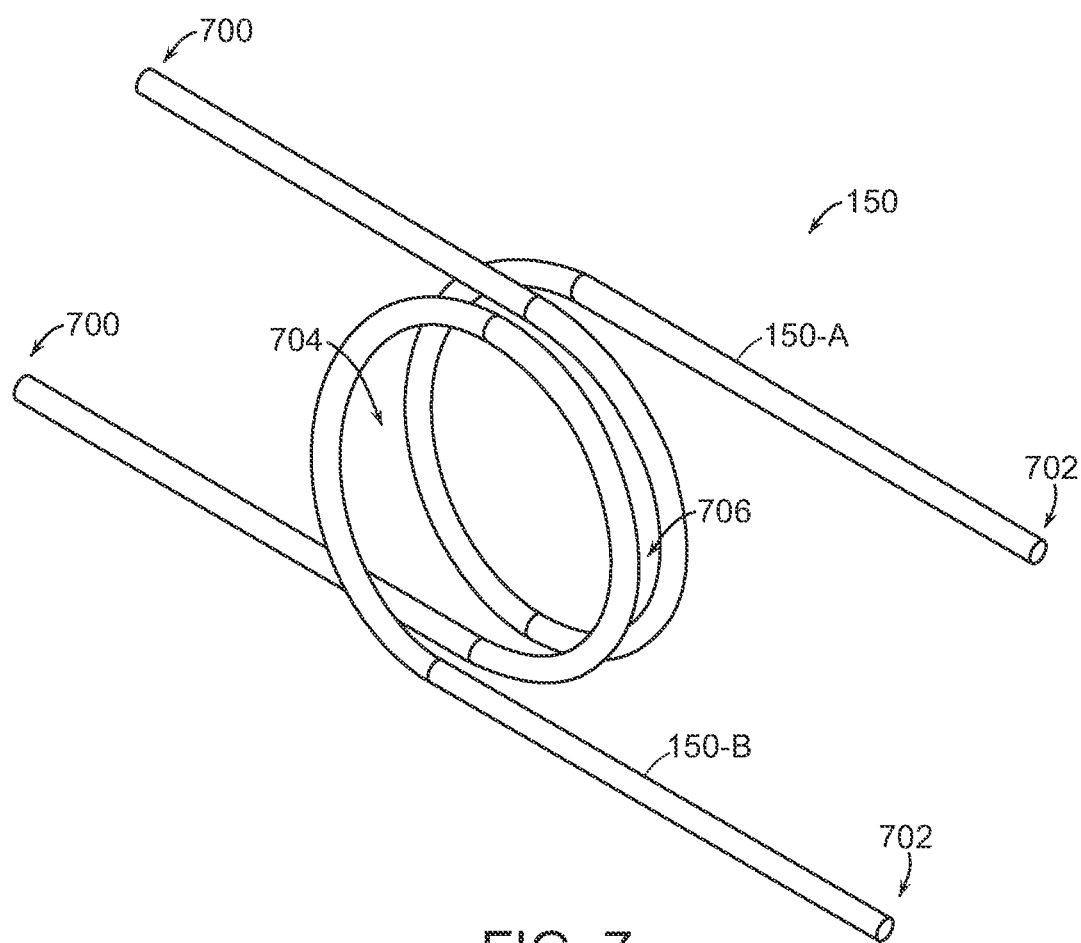
FIG. 7 is a perspective view of two filaments of a valve, each of the filaments forming a loop.
Figure 8:
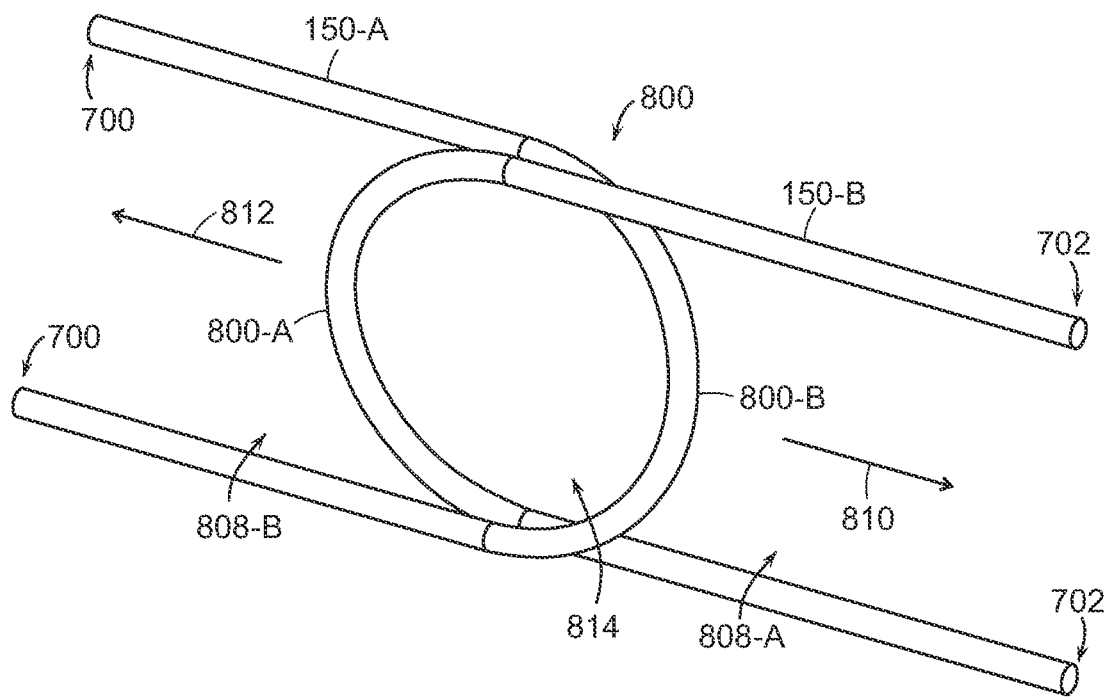
FIG. 8 is a perspective view of two overlapping and interlocked bights in an open configuration.
Figure 9:
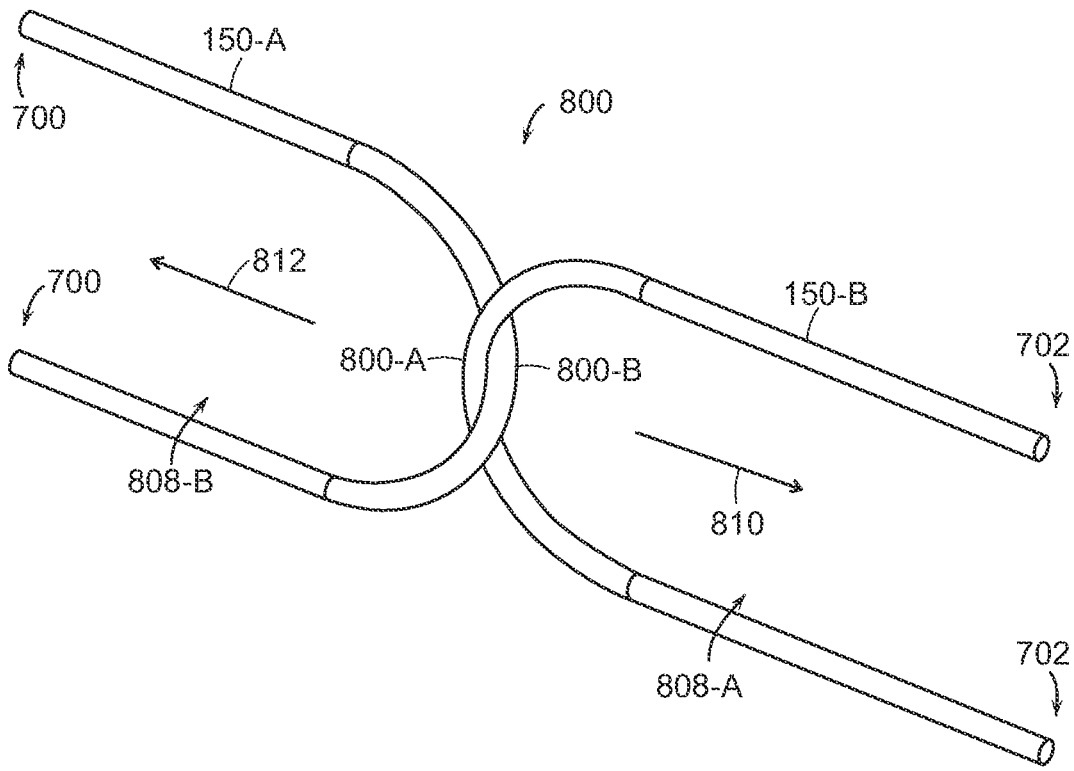
FIG. 9 is a perspective view of two overlapping and interlocked bights in a closed configuration.

In some embodiments, the filament 150 can comprise multiple filaments, and specifically, as shown in FIGS. 7 through 9, the filament 150 can comprise a first filament 150-A and a second filament 150-B. In embodiments in which the filament 150 comprises multiple filaments, each of the multiple filaments can have a first end 700 and a second end 702. The first and second filaments 150-A, 150-B can be coupled to the actuator 142. In such embodiments, the first and second ends 700, 702 can be coupled to the actuator 142 to move the filaments 150-A, 150-B between the first and second configurations and/or from the first configuration to the second configuration. In some embodiments, both of the first end 700 and the second end 702 of one or more of the multiple filaments 150 can be coupled to a single button 144, in some embodiments, each of the first end 700 and the second end 702 of one or more of the multiple filaments 150 can be coupled to different buttons 144, and in some embodiments, one of the first end 700 and the second end 702 of one or more of the multiple filaments 150 can be coupled to one button 144 and the other of the first end 700 and the second end 702 of those one or more filaments 150 can be coupled to the housing 128 or other portion of the valve 104.

The filament 150 can be arranged in a variety of configurations. In some embodiments, the filament 150 can be configured to form a single loop 604 that can extend around the elongate member 132 and/or through which the elongate member 132 can be received as shown in FIG. 6, and in some embodiments, the filament 150 can be configured to form multiple loops, and specifically a first loop 704 and a second loop 706 as shown in FIG. 7. The first and second loops 704, 706 can each receive the elongate member 132. In some embodiments, a diameter or size of the loop 604, or of the loops 704, 706 can decrease when the constricting mechanism 141 is moved from the second configuration to the first configuration.

In some embodiments, the filament 150 can be configured to form a bight 800, which bight 800 can be a single bight or multiple bights. As used herein, a "bight" refers to a U-shaped section between the two ends of the filament 150. As depicted in FIGS. 8 and 9, the bight 800 can comprise multiple bights, and specifically a first bight 800-A and a second bight 800-B. In some embodiments, the first bight 800-A can extend through the second bight 800-B such that the first and second bights 800-A, 800-B interlock, whereas in other embodiments, the first and second bights 800-A, 800-B can be non-interlocking. Similarly, in embodiments containing the filament 150 having multiple loops, one or several of the multiple loops can be interlocking.

In some embodiments, the bight 800, and specifically one or both of the first bight 800-A and the second bight 800-B can be formed around a portion of the elongate member 132 and/or can extend around a portion of the elongate member 132. Each bight 800 can define a partially enclosed receiving area 808 wherein the elongate member 132 can be received. Thus, the first bight 800-A can define a first receiving area 808-A and the second bight 800-B can define a second receiving area 808-B.

As seen in FIGS. 8 and 9, multiple bights, and specifically the first and the second bights 800-A, 800-B can be positioned and oriented such that the first bight 800-A has a first orientation or first direction as indicated by arrow 810, and the second bight has a second orientation or second direction as indicated by the arrow 812. In some embodiments, the first orientation is different from the second orientation such that the first and second receiving areas 808-A, 808-B overlap and define an encircled area 814, also referred to herein as a constricting area 814. The elongate member 132 can be received within the encircled area 814. In embodiments in which bights 800-A, 800-B overlap to define the encircled area 814, the movement of the constricting mechanism 141 to the first configuration can result in and/or include the first bight 800-A moving in the direction indicated by the arrow 810 and/or the second bight 800-B moving in the direction indicated by the arrow 812, which movement of the bights 800-A, 800-B decreases the size of the encircled area 814 and constricts, collapses, and/or seals the elongate member 132 extending through the encircled area 814.

The filament(s) 150 forming the bights 800 can each apply an arcuate line or narrow longitudinal zone of pressure to the elongate member 132. If the filament(s) are circular in cross-section, the zone of pressure can be very small, and can, in some embodiments, be less than the diameter or thickness of the filament. In some embodiments, the filaments have a diameter or width less than about 2.5 mm, less than about 2 mm, less than about 1.5 mm, less than about 1.25 mm, less than about 1 mm, less than about 0.75 mm, less than about 0.5 mm, and/or less than about 0.25 mm. In some embodiments, the filaments can have a diameter or width of between about 0.01 mm and 2.5 mm, between about 0.05 mm and 2 mm, between about 0.1 mm and 1 mm, and/or between about 0.125 mm and 0.70 mm. In some embodiments, the arcuate line or zone of pressure may form two opposing arcs and in other embodiments, the arcuate line of pressure may be a singular substantially circular line or zone that encircles the elongate member at least once. The longitudinal length of the of the line or zone of pressure may be very short compared to other valves known in the art. In some embodiments, the longitudinal length of the zone of pressure applied to the elongate member 132 by the filament(s) 150 may be less than about 2.0 mm and in some embodiments less than about 0.5 mm. In some embodiments, the filament(s) 150 can have any desired cross-sectional shape including, for example, a circular cross-section, a rectangular cross-section, an oval cross-section, a square cross-section, a polygonal cross-section, a triangular cross-section, or any other desired shape of cross-section.

Figure 10:
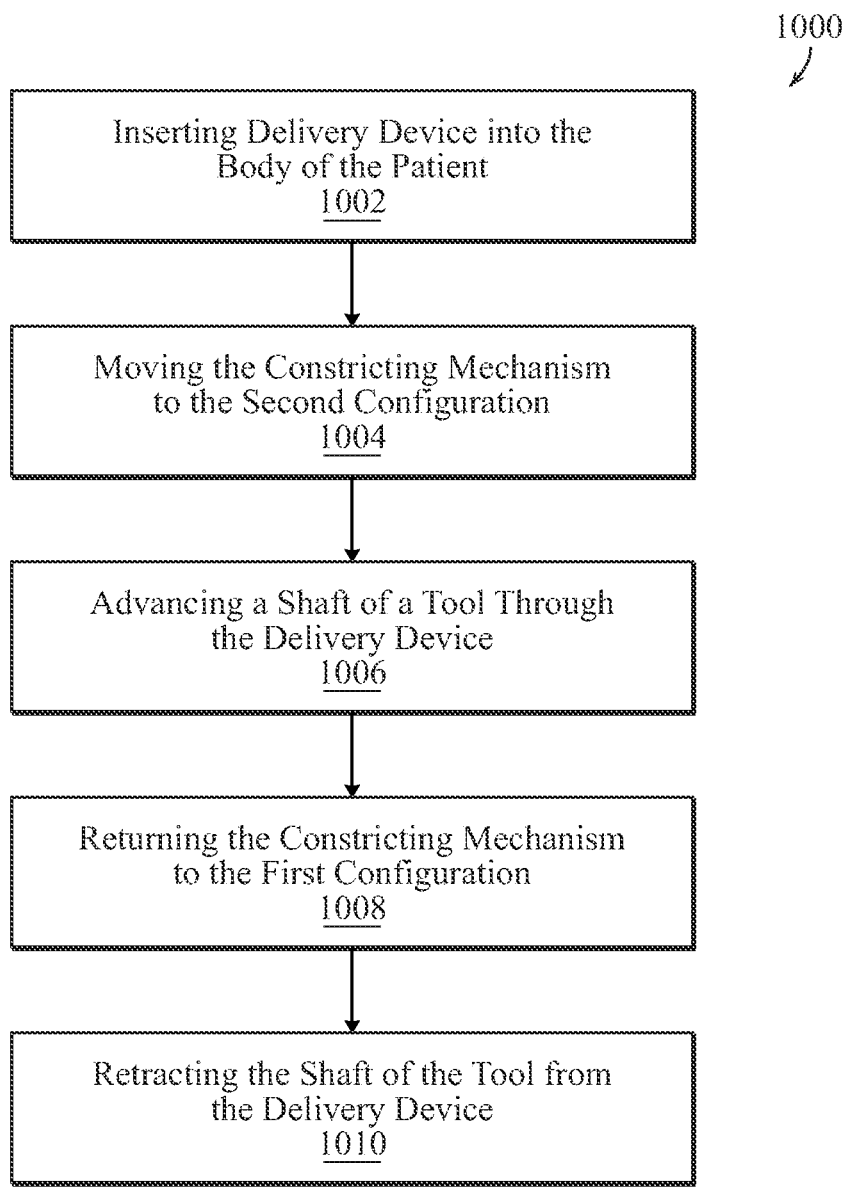
FIG. 10 is a flowchart illustrating one embodiment of a method for sealing a valve and/or catheter.

With reference now to FIG. 10, a flowchart illustrating one embodiment of a process 1000 for sealing a valve 104 and/or catheter 102 accessing a body of a patient is shown. The process 1000 can be performed using the valve 104 and/or the delivery system 100. The process 1000 begins at block 1002, wherein the delivery device 100, and specifically the catheter 102 of the delivery device 100 is inserted into the body of the patient. In some embodiments, this can include inserting the catheter 102 into a portion of the circulator system of the patient such as, for example, a blood vessel including an artery or a venous vessel. In some embodiments, the delivery device 100 can be inserted into the body of the patient directly through an aperture or incision in the patient, and in some embodiments, the delivery device 100 can be inserted into the body of the patient via another catheter or device. In some embodiments, the constricting mechanism 141 can be in the first configuration while the delivery device 100 and/or the catheter 102 is inserted into the patient's body.

After the delivery device 100 is inserted into the body of the patient, the process 1000 proceeds to block 1004, wherein the constricting mechanism 141 is moved from the first configuration to the second configuration. As described above, the central lumen 138 of the elongate member 132 is unsealed when the constricting mechanism 141 is in the second configuration. In some embodiments, the moving of the constricting mechanism 141 from the first configuration to the second configuration can include the manipulation of the actuator 142 and/or the control of the actuator 142, and specifically the depressing of the one or several buttons 144 to move the filament 150 from the first position to the second position to allow the expansion and opening of the central lumen 138 of the elongate member 132.

After the constricting mechanism 141 is moved from the first configuration to the second configuration, the process 1000 proceeds to block 1006, wherein the tool 400, and specifically the shaft 402 of the tool 400 is advanced through the delivery device 100 and specifically through the valve 104 until a first end of the tool reaches a desired position within the body of the patient. In some embodiments, a portion of the shaft 402 can be positioned within the central lumen 138 of the elongate member 132 after the advancing of the tool 400 through the delivery device 100. In some embodiments, after the tool 400 is advanced through the delivery device 100, the desired procedure can be performed with the tool.

After the tool 400 is advanced through the delivery device 100, or while the tool 400 is being advanced through the delivery device 100, the process 1000 proceeds to block 1008, wherein the constricting mechanism 141 is returned to the first configuration. In some embodiments, the returning of the constricting mechanism 141 to the first configuration can include the release of the one or several buttons 144 and/or the control of the actuator 142 to reconfigure the constricting mechanism 141 to the first configuration. In some embodiments, the return of the constricting mechanism 141 to the first configuration can result in the collapse and/or sealing of the elongate member 132 and specifically the central lumen 138 of the elongate member 132 around the tool 400 and specifically around the shaft 402 of the tool 400. The return of the constricting mechanism 141 to the first configuration, or the movement of the constricting mechanism 141 to the first configuration can include the decreasing of the size and/or diameter of one or several loops formed by the filament 150 and/or the movement of one or several bights 800 such as, for example, the movement of the first bight 800-A in the first direction indicated by arrow 810 and the movement of the second bight 800-B in the second direction indicated by arrow 812 to reduce the size of the constricting area 814. In some embodiments, after the constricting mechanism is returned to the first configuration, the desired procedure can be performed with the tool.

After the constricting mechanism is returned to the first configuration, the process 1000 proceeds to block 1010, wherein the tool 400, and specifically the shaft 402 of the tool 400 is retracted from the delivery device 100, and more specifically from the valve 104. In some embodiments, the valve 104 can remain sealed during the retracing of the tool 400 and/or the shaft 402 of the tool. In some embodiments, the valve 104 remains sealed during the retracting of the tool 400 and/or the retracting of the shaft 402 of the tool 400 as the constricting mechanism 141 can remain in the first configuration during the retracing of the tool 400 and/or the shaft 402 of the tool 400.

In some embodiments, the constricting mechanism 141 can be moved to the second configuration to allow the retraction of the tool 400 and/or the shaft 402 of the tool 400 from the valve 104, and the constricting mechanism 141 can be returned to the first configuration when the tool 400 and/or the shaft 402 of the tool 400 is removed from the valve 104. In some embodiments, the retraction of the tool 400 and/or shaft 402 of the tool 400 from the valve 104 can be performed with the constricting mechanism 141 left in the first configuration. In some embodiments, the constricting mechanism 141 can be moved to the second configuration, and then returned to the first configuration via the manipulation and/or control of the actuator 142, which manipulation and/or control of the actuator 142 can include the depressing of the one or several buttons 144 to move the constricting mechanism 141 to the second configuration, and the release of the one or several buttons 144 to return the constricting mechanism 141 to the first configuration. In some embodiments, if the procedure is complete, the delivery device 100 can then be removed from the body of the patient, and any incision created for the procedure can be closed.

Figure 11:
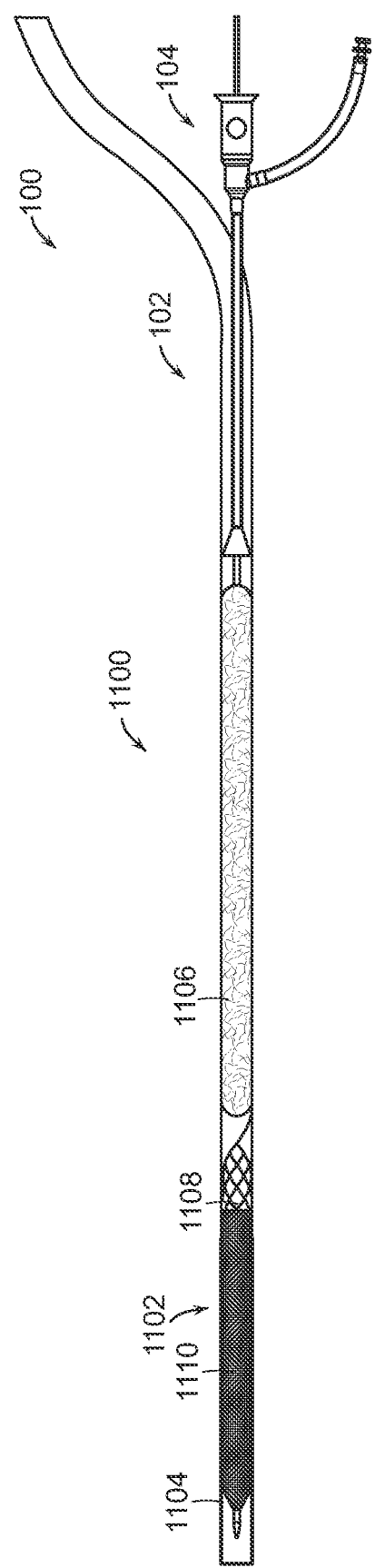
FIG. 11 is a side view of one embodiment of a thrombectomy system including the delivery device.

With reference now to FIG. 11, a side view of one embodiment of a thrombectomy system 1100 including the delivery device 100 and a thrombus extraction device 1102 is shown. In some embodiments, the thrombectomy system 1100 can be used to access a blood vessel 1104 to treat and/or extract a thrombus 1106 from the blood vessel 1104. The thrombus extraction device 1102 can include a self-expanding coring element 206 and expandable cylindrical portion 208. In some embodiments, and as shown in FIG. 11, the thrombus extraction device 1102 can be the tool 400 that can extend through the valve 104, and in some embodiments, the valve 104 can be a part of the thrombus extraction device 1102. Further details of thrombectomy systems, thrombus extraction devices, and methods of using the same are disclosed in: U.S. application Ser. No. 15/268,296, filed Sep. 16, 2016, and entitled "INTRAVASCULAR TREATMENT OF VASCULAR OCCLUSION AND ASSOCIATED DEVICES, SYSTEMS, AND METHODS"; U.S. application Ser. No. 15/498,320, filed Apr. 26, 2017, and entitled "DEVICES AND METHODS FOR TREATING VASCULAR OCCLUSION"; and U.S. application Ser. No. 15/466,740, filed on Mar. 22, 2017, and entitled "DEVICE AND METHOD FOR TREATING VASCULAR OCCLUSION", the entirety of each of which is hereby incorporated by reference herein.

Figure 12:
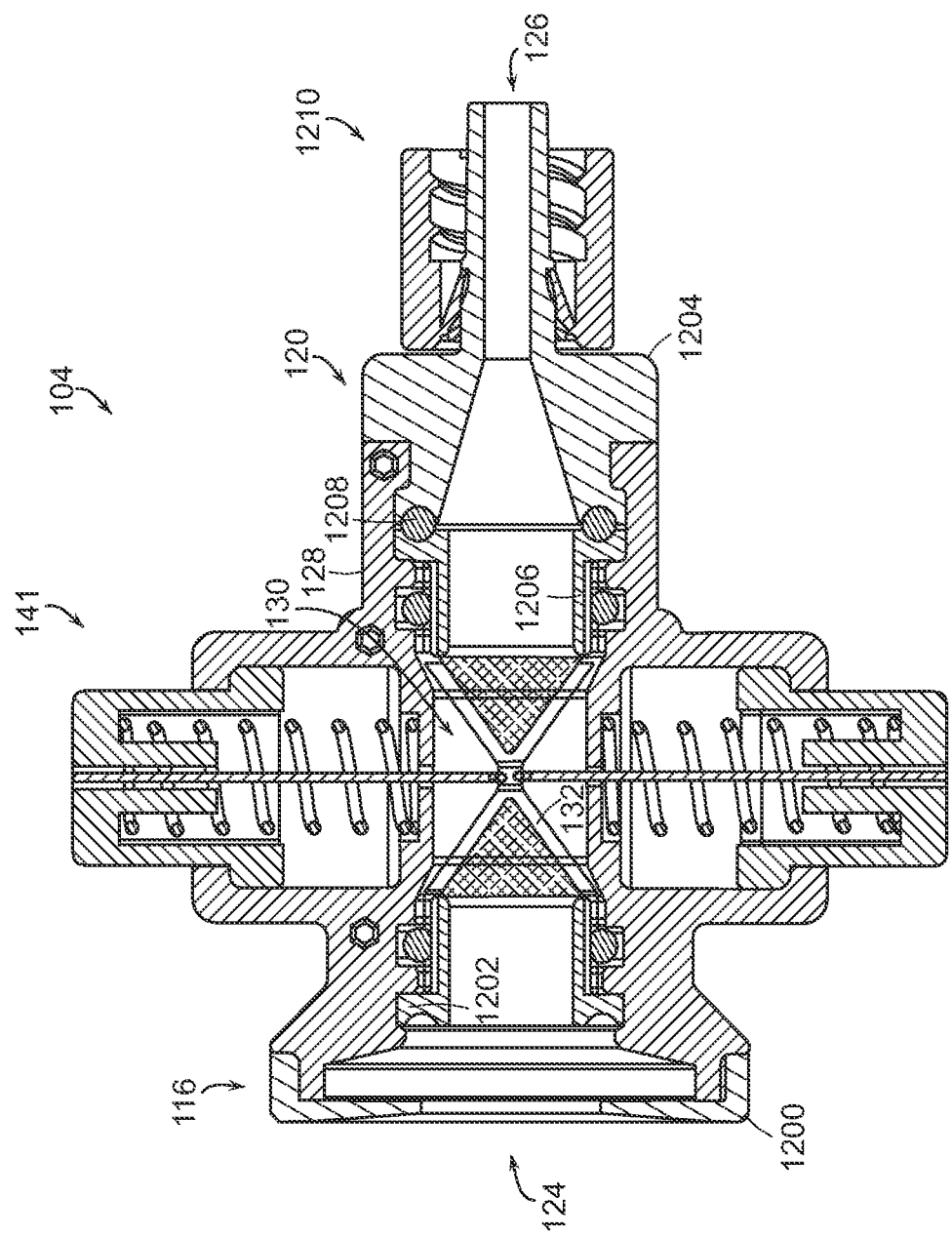
FIG. 12 is a side-section view of another embodiment of a hemostasis valve having two-piece caps.

With reference now to FIG. 12, a side-section view of another embodiment of the hemostasis valve 104 having two piece caps 116, 120 is shown. The valve 104 can include a housing 128 defining an interior channel 130 through which the tubular member 132 can extend. The valve 104 can include the proximal cap 116 and the distal cap 120. In some embodiments, the proximal cap 116 can comprise a two piece cap and can include a proximal exterior member 1200 and a proximal channel member 1202. In some embodiments, the distal cap 120 can comprise a two-piece cap and can include a distal exterior member 1204 and a distal channel member 1206. In some embodiments, this coupling between the proximal exterior member 1200 and the proximal channel member 1202 and/or the coupling between the distal exterior member 1204 and the distal channel member 1206 can be a sealed coupling so as to prevent the leakage of material including fluid or gas between the respective ones of the proximal exterior member 1200 and the proximal channel member 1202 and/or the distal exterior member 1204 and the distal channel member 1206. In some embodiments, this sealing coupling can be achieved and/or maintained via a seal such as an O-ring 1208 that can be positioned between the proximal exterior member 1200 and the proximal channel member 1202 and/or between the distal exterior member 1204 and the distal channel member 1206.

In some embodiments, the proximal exterior member 1200 can be coupled, and in some embodiments, rotatingly coupled to the proximal channel member 1202 in a manner to allow the rotation of the proximal exterior member 1200 without rotating the proximal channel member 1202. Similarly, in some embodiments, the distal exterior member 1204 can be rotatingly coupled to the distal channel member 1206 in a manner to allow the rotation of the distal exterior member 1204 without the rotating of the distal channel member 1206. In some such embodiments, the channel members 1202, 1206 can be non-rotatable with respect to the housing 128 and/or the tubular member 132, and one or both of the exterior members 1200, 1204 can be rotatable with respect to the housing 128 and/or the tubular member 132. In such an embodiment, the maintaining of the rotational position of the channel members 1202, 1206 with respect to the housing 128 and/or the tubular member 132 can prevent the twisting of the tubular member 132 which can result in the sealing of the tubular member 132 regardless of the configuration of the constructing mechanism 141.

The exterior members 1200, 1204 can comprise a variety of shapes and sizes and can include a variety of features. In some embodiments, one or both of the exterior members 1200, 1204 can be coupled to, for example, a shaft similar to the shaft 106 shown in FIG. 1. In some embodiments, for example, the distal exterior member 1204 can be coupled to a shaft 106, including, for example, can be non-detachably coupled to the shaft 106. In some embodiments, one or both of the exterior members can include one or several features configured to facilitate coupling with the valve 104. These one or several features can include, for example, one or several male or female: connectors; couplers; attachment mechanisms; or the like. In some embodiments, these one or several features can facilitate use of the valve with other existing components, instruments, tools, or the like. In some embodiments, for example, one or both of the exterior members 1200, 1204 can comprise either a male or female luer fitting, and specifically as shown in FIG. 12, the distal exterior member 1204 can comprise a male luer fitting 1210.

Several aspects of the present technology are set forth in the following examples.

1. A hemostatic valve for sealing a medical device, the hemostatic valve comprising:
   an elongate member having a first end, a second end, and a central lumen extending therebetween, wherein the elongate member is pliable;
   a reinforcement structure extending along at least a portion of the elongate member, wherein the reinforcement structure is coupled to the elongate member; and
   an active tensioning mechanism coupled to the elongate member, wherein the tensioning mechanism is moveable between a first configuration wherein the central lumen is constricted and sealed and a second configuration wherein the central lumen is open.
2. The hemostatic valve of example 1, wherein the elongate member comprises a compliant polymer tube.
3. The hemostatic valve of example 1 or 2, wherein the tensioning mechanism comprises at least one filament extending at least partially around the elongate member.
4. The hemostatic valve of example 3, wherein the reinforcement structure is positioned between the at least one filament and the elongate member.
5. The hemostatic valve of example 4, wherein the reinforcement structure comprises a braided mesh.
6. The hemostatic valve of example 4 or 5, wherein the reinforcement structure is coupled to the elongate member at a position proximate to the first end of the elongate member and at a position proximate to the second end of the elongate member.
7. The hemostatic valve of example 6, wherein the reinforcement structure is not coupled to the elongate member at a position between the first end of the elongate member and the second end of the elongate member.
8. The hemostatic valve of any one of examples 3-7, wherein the tensioning mechanism comprises an actuator coupled to the at least one filament, wherein the actuator is moveable to control movement of the at least one filament from a first position wherein the central lumen is constricted and sealed to a second position wherein the central lumen is open, wherein the at least one filament is in the first position when the tensioning mechanism is in the first configuration.
9. The hemostatic valve of example 8, wherein the actuator is biased towards the first position.
10. The hemostatic valve of example 8 or 9, wherein the actuator is biased toward the second position.
11. The hemostatic valve of any one of examples 8-10, wherein the actuator comprises a manual actuator.
12. The hemostatic valve of any one of examples 8-11, wherein the at least one filament forms a loop around the elongate member.
13. The hemostatic valve of any one of examples 8-12, wherein the at least one filament forms a bight around a portion of the elongate member.
14. The hemostatic valve of any one of examples 8-13, wherein the at least one filament comprises a first filament and a second filament, wherein each of the first filament and the second filament are coupled to the actuator, and wherein the first filament and the second filament are moveable from the first position to the second position.
15. The hemostatic valve of example 14, wherein each of the first filament and the second filament form a loop around the elongate member.
16. The hemostatic valve of example 14 or 15, wherein the first filament forms a first bight around a first portion of the elongate member, and wherein the second filament forms a second bight around a second portion of the elongate member.
17. The hemostatic valve of example 16, wherein the first bight extends through the second bight.
18. The hemostatic valve of any one of examples 1-17, further comprising a shell defining a first aperture and a second aperture, wherein the elongate member extends from the first aperture to the second aperture and fluidly couples the first aperture and the second aperture.
19. The hemostatic valve of any one of examples 1-18, wherein the tensioning mechanism is self-adjustable to seal around tools of different sizes extending through the hemostatic valve.
20. The hemostatic valve of any one of examples 1-19, wherein the central lumen comprises a single lumen.
21. The hemostatic valve of any one of examples 1-20, wherein the central lumen comprises a plurality of lumens.
22. A delivery system for intravascular access of a blood vessel within a patient's body, the delivery system comprising:
   a catheter having a first end, a second end, and a catheter lumen extending therebetween;
   a hemostatic valve coupled to the first end of the catheter, the hemostatic valve comprising:
      a tubular member having a first end, a second end, and a central lumen extending therebetween, wherein the central lumen of the tubular member is fluidly coupled with the catheter lumen; and
      an active tensioning mechanism coupled to the tubular member, the tensioning mechanism moveable between a first configuration wherein the tensioning mechanism constricts on the central lumen and the central lumen is sealed and a second configuration wherein the central lumen is open.
23. The delivery system of example 22, wherein the hemostatic valve further comprises a reinforcement structure extending along at least a portion of the tubular member.
24. The delivery system of example 22 or 23, wherein the reinforcement structure is located between the tensioning mechanism and the tubular member.
25. The delivery system of example 24, wherein the reinforcement structure comprises a braided mesh.
26. The delivery system of example 24 or 25, wherein the reinforcement structure is coupled to the tubular member at a position proximate to the first end of the tubular member and at a position proximate to the second end of the tubular member.
27. The delivery system of example 26, wherein the reinforcement structure is adhered to the tubular member at the first end of the tubular member and at the second end of the tubular member.
28. The delivery system of example 27, wherein the reinforcement structure is uncoupled to the tubular member between the first end of the tubular member and the second end of the tubular member.
29. The delivery system of any one of examples 22-28, wherein the tensioning mechanism comprises at least one filament extending at least partially around the tubular member.
30. The delivery system of example 29, wherein the tensioning mechanism comprises an actuator coupled to the at least one filament, wherein moving the tensioning mechanism from the first configuration to the second configuration comprises moving the actuator and the thereto coupled at least one filament from a first position to a second position, wherein the filament constricts and seals the central lumen of the tubular member when the filament is in the first position.
31. The delivery system of example 30, wherein the actuator comprises a manual actuator.
32. The delivery system of example 31, wherein the actuator comprises a pair of opposing and depressable buttons, wherein the buttons are biased towards an undepressed position.
33. The delivery system of example 31 or 32, wherein the central lumen is sealed when the buttons are in the undepressed position.
34. The delivery system of any one of examples 30-33, wherein the filament comprises a monofilament.
35. The delivery system of any one of examples 30-34, wherein the filament comprises at least one of: a polymer filament; or a metallic filament.
36. The delivery system of any one of examples 22-35, wherein the catheter comprises a thrombus extraction device.
37. A method of sealing a delivery device accessing a blood vessel of a patient, the method comprising:
inserting the delivery device comprising a catheter and a hemostatic valve into the blood vessel of the patient, the catheter having a first end, a second end, and a catheter lumen extending therethrough, and the hemostatic valve coupled to the first end and having a tubular member defining a central lumen fluidly coupled with the catheter lumen and a tensioning mechanism coupled with the tubular member, wherein the tensioning mechanism collapses and seals the central lumen in a first configuration and thereby seals access to the blood vessel;
moving the tensioning mechanism of the hemostatic valve to a second configuration, wherein the central lumen is open and access to the blood vessel is unsealed when the tensioning mechanism is in the second configuration;
advancing a shaft of a tool through the delivery device until a first end of the tool reaches a desired position within the blood vessel of the patient and a portion of the shaft is positioned within the central lumen of the tubular member; and
returning the tensioning mechanism of the hemostatic valve to the first configuration such that the tubular member collapses on the shaft of the tool and seals around the shaft of the tool.
38. The method of example 37, further comprising retracting the shaft of the tool from the delivery device.
39. The method of example 38, wherein the tensioning mechanism is maintained in the first configuration during and after the retracting of the shaft of the tool from the delivery device.
40. The method of example 38 or 39, wherein the tensioning mechanism is moved to the second configuration during the retracting of the shaft of the tool from the delivery device, and wherein the tensioning mechanism is returned to the first configuration after the shaft of the tool is retracted from the delivery device.
41. The method of any one of examples 37-40, wherein the tensioning mechanism comprises at least one filament extending at least partially around the tubular member, wherein the at least one filament collapses the tubular member when the tensioning mechanism is in the first configuration.
42. The method of example 41, wherein the at least one filament circumferentially constricts the tubular member to collapse the tubular member when the tensioning mechanism is in the first configuration.
43. The method of example 41 or 42, wherein the hemostatic valve comprises a reinforcement structure located between the at least one filament and the tubular member.
44. The method of any one of examples 41-43, wherein the at least one filament forms a loop around the elongate member, and wherein moving the tensioning mechanism from the second configuration to the first configuration reduces a size of the loop to thereby constrict the tubular member within the loop.
45. The method of any one of examples 41-44, wherein the filament forms at least one bight around a portion of the elongate member.
46. The method of example 45, wherein the filament comprises a first filament and a second filament, and wherein the at least one bight comprises a first bight oriented in a first direction and formed by the first filament and a second bight oriented in a second direction and formed by the second filament, wherein the first and second bights overlap to encircle a portion of the tubular member within an constricting area.
47. The method of example 46, wherein moving the tensioning mechanism from the second configuration to the first configuration comprises moving the first bight in the first direction and the second bight in the direction to reduce the size of the constricting area and collapse and seal the central lumen of the tubular member.
48. The method of any one of examples 37-47, wherein the tensioning mechanism comprises an actuator, and wherein moving the tensioning mechanism to the second configuration comprises manipulating the actuator.

49. The method of any one of examples 37-48, further comprising applying a vacuum to the delivery device to aspirate material through the catheter, wherein the central lumen remains sealed during the aspiration.

50. The method of any one of examples 37-49, wherein the tool comprises a thrombus extraction device.

51. A hemostatic valve for sealing a medical device, the hemostatic valve comprising:
an elongate member having a first end, a second end, and a central lumen comprising a plurality of lumens extending therebetween, wherein the elongate member is pliable; and
an active tensioning mechanism coupled to the elongate member, wherein the tensioning mechanism is moveable between a first configuration wherein the central lumen is constricted and sealed and a second configuration wherein the central lumen is open.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

In the previous description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

The invention claimed is:

1. A hemostasis valve, comprising:
a support;
an actuator having at least a first member movably coupled to the support;
a collapsible tubular sidewall defining a lumen carried by the support;
a filament formed in a loop around the tubular sidewall, the filament having at least a first end portion extending away from the loop to the first member; and
a spring configured to move the first member in a direction that pulls the first end portion away from the tubular sidewall, reducing a diameter of the lumen in response to reducing a diameter of the loop.

2. The hemostasis valve of claim 1, further comprising a second member movably coupled to the support.

3. The hemostasis valve of claim 2 wherein the filament further comprises a second end portion extending away from the loop to the second member.

4. The hemostasis valve of claim 3 wherein the first end portion, the loop, and the second end portion are one continuous filament.

5. The hemostasis valve of claim 3 wherein first member and the second member are biased in a direction that places the first end portion and the second end portion under sufficient tension to reduce the diameter of the lumen and provide a seal around a device extending through the lumen.

6. The hemostasis valve of claim 3 wherein the first member and the second member are biased in a direction that places the first end portion and the second end portion under sufficient tension to close the lumen.

7. The hemostasis valve of claim 1 wherein the lumen extends along a longitudinal axis, and wherein the direction is a direction away from the longitudinal axis.

8. The hemostasis valve of claim 1 wherein the lumen extends along a longitudinal axis, and wherein the direction is a direction orthogonal to the longitudinal axis.

9. The hemostasis valve of claim 1 wherein the spring is positioned between the first member and the support.

10. The hemostasis valve of claim 1 wherein the first member is a button.

11. The hemostasis valve of claim 10 wherein the direction is a first direction, and wherein the button is depressible in a second direction to move the first end portion toward the tubular sidewall to increase the diameter of the lumen in response to increasing the diameter of the loop.

12. The hemostasis valve of claim 1 wherein the direction is a first direction, and wherein the first member is actuatable in a second direction to move the first end portion toward the tubular sidewall to increase the diameter of the lumen in response to increasing the diameter of the loop.

13. The hemostasis valve of claim 12 wherein the first direction is opposite the second direction.

14. The hemostasis valve of claim 13 wherein the lumen extends along a longitudinal axis, and wherein the first direction and the second direction are orthogonal to the longitudinal axis.

15. The hemostasis valve of claim 1 wherein the actuator further comprises a second member movably coupled to the support, wherein the filament further comprises a second end portion extending away from the loop to the second member, wherein the spring is a first spring, wherein the direction is a first direction, and further comprising a second spring configured to move the second member in a second direction that pulls the second end portion away from the tubular sidewall, reducing the diameter of the lumen in response to reducing the diameter of the loop.

16. The hemostasis valve of claim 15 wherein the first direction is opposite to the second direction.

17. The hemostasis valve of claim 15 wherein the first member is actuatable in the second direction and/or the second member is actuatable in the first direction to move the first end portion toward the tubular sidewall to increase the diameter of the lumen in response to increasing the diameter of the loop.

18. An aspiration catheter system, comprising:
an aspiration catheter defining a lumen and having a proximal end portion; and
a hemostasis valve comprising—
  a support;
  an actuator having at least a first member movably coupled to the support;
  a collapsible tubular sidewall defining a lumen carried by the support, wherein the lumen of the tubular sidewall is selectively fluidly couplable to the lumen of the aspiration catheter;
  a filament formed in a loop around the tubular sidewall, the filament having at least a first end portion extending away from the loop to the first member; and
  a spring configured to move the first member in a direction that pulls the first end portion away from the tubular sidewall, reducing a diameter of the lumen in response to reducing a diameter of the loop to fluidly decouple the lumen of the tubular sidewall from the lumen of the aspiration catheter.

19. The aspiration catheter system of claim 1 wherein the direction is a first direction, and wherein the first member is actuatable in a second direction to move the first end portion toward the tubular sidewall to increase the diameter of the lumen in response to increasing the diameter of the loop to fluidly couple the lumen of the tubular sidewall to the lumen of the aspiration catheter.

20. A hemostasis valve, comprising:
a support;
a button movably coupled to the support;
a collapsible tubular sidewall carried by the support and defining a lumen;
a filament formed in a loop around the tubular sidewall, the filament having at least a first end portion extending away from the loop to the button; and
a biasing member positioned between the support and the button, wherein the biasing member is configured to bias the button in a direction that pulls the first end portion away from the tubular sidewall to reduce a diameter of the loop to thereby reduce a diameter of the lumen.

* * * * *